US012569420B2

(12) United States Patent
Cottard-Mei

(10) Patent No.: US 12,569,420 B2
(45) **Date of Patent: *Mar. 10, 2026**

(54) COMPOSITION COMPRISING A PARTICULAR OXIDATION DYEING BASE AND AT LEAST TWO PARTICULAR COUPLERS

(71) Applicant: L'Oreal, Paris (FR)

(72) Inventor: Laurence Cottard-Mei, Saint-Ouen (FR)

(73) Assignee: L'Oréal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 18/253,820

(22) PCT Filed: Dec. 16, 2021

(86) PCT No.: PCT/EP2021/086287
§ 371 (c)(1),
(2) Date: May 22, 2023

(87) PCT Pub. No.: WO2022/129394
PCT Pub. Date: Jun. 23, 2022

(65) Prior Publication Data

US 2024/0000685 A1 Jan. 4, 2024

(30) Foreign Application Priority Data

Dec. 17, 2020 (FR) ...................................... 2013507

(51) Int. Cl.
*A61Q 5/10* (2006.01)
*A61K 8/41* (2006.01)
*A61K 8/49* (2006.01)

(52) U.S. Cl.
CPC ................ *A61K 8/415* (2013.01); *A61K 8/49* (2013.01); *A61Q 5/10* (2013.01); *A61K 2800/4324* (2013.01); *A61K 2800/882* (2013.01)

(58) Field of Classification Search
CPC .. A61K 8/415; A61K 8/49; A61K 2800/4324; A61K 2800/882; A61K 8/411; A61K 8/31; A61Q 5/10
USPC .............................................................. 8/405
See application file for complete search history.

(56) References Cited

U.S. PATENT DOCUMENTS 3,589,978 A 6/1971 Kamal et al.
4,003,699 A 1/1977 Rose et al.
4,013,307 A 3/1977 Dowd et al.
4,137,180 A 1/1979 Naik et al.
RE30,199 E 1/1980 Rose et al.
4,333,730 A 6/1982 Bugaut et al.
4,823,985 A 4/1989 Grollier et al.
4,874,554 A 10/1989 Lange et al.
5,061,289 A 10/1991 Clausen et al.
5,380,340 A 1/1995 Neunhoeffer et al.
5,534,267 A 7/1996 Neunhoeffer et al.
5,663,366 A 9/1997 Neunhoeffer et al.
5,766,576 A 6/1998 Löwe et al.
6,099,592 A 8/2000 Vidal et al.
6,099,593 A 8/2000 Terranova et al.
6,284,003 B1 9/2001 Rose et al.
11,213,471 B2 1/2022 Nicou et al.
2014/0053345 A1* 2/2014 Rapold .................. A61K 8/342 8/408
2014/0082855 A1* 3/2014 Rapold .................. A61K 8/062 8/405
2015/0335563 A1 11/2015 Allard et al.
2017/0165166 A1 6/2017 Gebert-Schwarzwaelder et al.
2017/0258695 A1* 9/2017 Consoli .................... A61K 8/55
2019/0117541 A1* 4/2019 Consoli .................... A61K 8/44

FOREIGN PATENT DOCUMENTS

CA 2576189 A1 6/2007
CA 2615230 A1 4/2008
DE 2359399 A1 6/1975
DE 3843892 A1 6/1990
DE 4133957 A1 4/1993
DE 19543988 A1 5/1997
EP 0317542 A2 5/1989
EP 0399133 A1 11/1990
EP 0509382 A2 10/1992
EP 0516102 A1 12/1992
EP 0770375 A1 5/1997
EP 3287120 A1 * 2/2018
EP 3295923 A1 * 3/2018 ............... A61Q 5/10
EP 3295924 A1 3/2018
FR 2586913 A1 3/1987
FR 2733749 A1 11/1996
FR 2750048 A1 12/1997

(Continued)

OTHER PUBLICATIONS

International Search Report and Written Opinion for counterpart Application No. PCT/EP2021/086287, dated May 18, 2022.

(Continued)

*Primary Examiner* — Eisa B Elhilo
(74) *Attorney, Agent, or Firm* — The Marbury Law Group, PLLC

(57) ABSTRACT

Composition comprising a particular oxidation dyeing base and at least two particular couplers. The invention relates to a composition comprising at least one particular oxidation dyeing base and at least two particular couplers. The invention also relates to a process for dyeing keratin fibres, in particular the hair, using this composition.

18 Claims, No Drawings

(56) References Cited

FOREIGN PATENT DOCUMENTS

| | | | | | |
|---|---|---|---|---|---|
| FR | 2988591 | A1 | | 10/2013 | |
| FR | 3045379 | A1 | | 6/2017 | |
| GB | 1026978 | A | | 4/1966 | |
| GB | 1153196 | A | | 5/1969 | |
| JP | 02-019576 | A | | 1/1990 | |
| JP | 05-163124 | A | | 6/1993 | |
| WO | 94/08969 | A1 | | 4/1994 | |
| WO | 94/08970 | A1 | | 4/1994 | |
| WO | 96/15765 | A1 | | 5/1996 | |
| WO | 2016/097208 | A1 | | 6/2016 | |
| WO | WO 2018053177 | A1 | * | 3/2018 | ............... A61Q 5/10 |
| WO | 2022/129389 | A1 | | 6/2022 | |
| WO | 2022/129393 | A1 | | 6/2022 | |

OTHER PUBLICATIONS

Porter, M.R., "Handbook of Surfactants," published by Blackie & Son (Glasgow and London), 1991, pp. 116-178.
Todd, Charles, et al., "Volatile Silicone Fluids for Cosmetic Formulations," Cosmetics and Toiletries, vol. 91, Jan. 1976, pp. 29-32.
Non-Final Office Action in U.S. Appl. No. 18/037,247, mailed Aug. 16, 2024, 7 pages.
Scientific and Technical Information Center, EIC Search Report in U.S. Appl. No. 18/037,247, mailed Jul. 25, 2024, 83 pages.
International Search Report and Written Opinion for counterpart Application No. PCT/EP2021/086279, dated Mar. 24, 2022.
International Search Report and Written Opinion for counterpart Application No. PCT/EP2021/086285, dated May 13, 2022.

* cited by examiner

COMPOSITION COMPRISING A PARTICULAR OXIDATION DYEING BASE AND AT LEAST TWO PARTICULAR COUPLERS

CROSS REFERENCE TO RELATED APPLICATIONS

This is a National Stage Application of PCT/EP2021/086287, filed internationally on Dec. 16, 2021, which claims priority to French Application No. 2013507, filed Dec. 17, 2020, both of which are incorporated by reference herein in their entireties.

The invention relates to a composition comprising at least one particular oxidation dyeing base and at least two particular couplers.

The invention also relates to a process for dyeing keratin fibres, in particular the hair, using this composition.

Finally, the invention relates to the use of such a composition for dyeing keratin fibres, and in particular the hair.

Many people have sought for a long time to modify the colour of their hair and in particular to mask their grey hair.

It is known practice to dye keratin fibres, in particular human keratin fibres such as the hair, to obtain permanent colourings with dyeing compositions containing oxidation dye precursors, in particular oxidation bases, such as ortho- or para-phenylenediamines, ortho- or para-aminophenols, or heterocyclic compounds such as pyrazoles, pyrazolinones or pyrazolo-pyridines. These oxidation bases are colourless or weakly coloured compounds which, when combined with oxidizing products, can give rise to coloured compounds via a process of oxidative condensation.

It is also possible to vary the shades obtained with these oxidation bases by combining them with couplers or colour modifiers. The variety of molecules used as oxidation bases and couplers allows a wide range of colours to be obtained. However, the use of these dye compositions may have a certain number of drawbacks.

Specifically, after application to keratin fibres, the dyeing power obtained may not be entirely satisfactory, or may even be weak, and lead to a restricted range of colours.

The colourings may also be insufficiently persistent with respect to external agents such as light, shampoo or perspiration, and may also be too selective, i.e. the difference in colouring is too great along the same keratin fibre that is differently sensitized between its end and its root.

By way of example, 2-(methoxymethyl)benzene-1,4-diamine, which is described in the document CA2576189 and which is known to be a dye precursor of interest, does not make it possible to achieve entirely satisfactory dyeing properties, in particular in terms of selectivity. Specifically, it does not make it possible to obtain a colour result which is uniform from the root to the end. In addition, it does not make it possible to ensure good coverage of the keratin fibres, and in particular of depigmented keratin fibres, such as grey hair. Furthermore, its dyeing power proves to be too limited, thus leading to a restricted dyeing range.

Thus, there is a real need to provide a composition for dyeing keratin fibres, in particular human keratin fibres such as the hair, which does not have the drawbacks mentioned above, i.e. which is capable of resulting in a good colour build-up and a strong colouring while at the same time having a low selectivity and a good fastness, and which is capable of resulting in good dyeing performance, even after a period of storage.

These aims and others are achieved by the present invention, one subject of which is thus a composition comprising:

2-(methoxymethyl)benzene-1,4-diamine of formula (I), its addition salts, its solvates and/or the solvates of its salts:

(I)

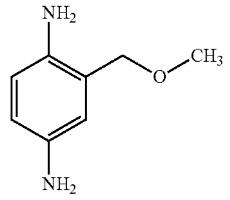

at least one coupler chosen from: 6-hydroxybenzomorpholine of formula (II), its addition salts, its solvates and/or the solvates of its salts, and mixtures thereof; and (II)

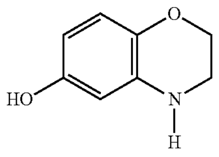

at least one coupler chosen from: 2-amino-5-ethylphenol of formula (III), its addition salts, its solvates and/or the solvates of its salts, and mixtures thereof (III)

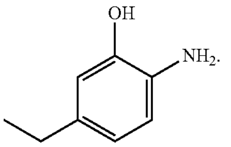

According to a preferred embodiment, the composition according to the invention is a composition for dyeing keratin fibres, in particular the hair.

The composition according to the invention may especially lead to chromatic, powerful, intense and sparingly selective colourings, i.e. colourings that are uniform along the length of the fibre. It also allows various shades to be achieved in a very wide range of colours. Furthermore, it enables a good colour build-up.

This composition also gives particularly good coverage of depigmented keratin fibres such as grey hair.

A subject of the invention is also a kit comprising, in a first compartment, a composition as defined above and, in a second compartment, an oxidizing composition comprising at least one chemical oxidizing agent.

According to the invention, the term "chemical oxidizing agent" is intended to mean an oxidizing agent other than atmospheric oxygen.

Other subjects, characteristics, aspects and advantages of the invention will become even more clearly apparent on reading the description and the examples which follow.

In that which follows, and unless otherwise indicated, the limits of a range of values are included in this range, in particular in the expressions "of between" and "ranging from . . . to . . . ".

Moreover, the expression "at least one" used in the present description is equivalent to the expression "one or more".

Oxidation Bases

The composition according to the invention comprises at least one particular oxidation base.

The composition according to the invention comprises at least 2-(methoxymethyl)benzene-1,4-diamine of formula (I), one of its addition salts, its solvates and/or the solvates of its salts.

The addition salts of the compound of formula (I) present in the composition according to the invention are chosen especially from the addition salts with an acid, such as the hydrochlorides, hydrobromides, sulfates, citrates, succinates, tartrates, lactates, tosylates, benzenesulfonates, phosphates and acetates, and the addition salts with a base such as sodium hydroxide, potassium hydroxide, aqueous ammonia, amines or alkanolamines.

Moreover, the solvates of the compound of formula (I) more particularly represent the hydrates of said compound and/or the combination of said compound with a linear or branched C1 to C4 alcohol such as methanol, ethanol, isopropanol or n-propanol. Preferably, the solvates are hydrates.

The total content of 2-(methoxymethyl)benzene-1,4-diamine of formula (I), of one of its addition salts, of its solvates and/or of the solvates of its salts preferably ranges from to 20% by weight, more preferentially from 0.005% to 15% by weight, better still from 0.01% to 10% by weight, even better still from 0.05% to 5% by weight, better yet from 0.1% to 3% by weight, relative to the total weight of the composition.

The composition according to the invention may optionally further comprise one or more additional oxidation bases different from the compound of formula (I), chosen from para-phenylenediamines, bis(phenyl)alkylenediamines, para-aminophenols, ortho-aminophenols and heterocyclic bases, their addition salts and their solvates.

Among the para-phenylenediamines different from the compound of formula (I), mention may be made, for example, of para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(3-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl) pyrrolidine, their addition salts with an acid and their solvates.

Among the bis(phenyl)alkylenediamines, mention may for example be made of N,N'-bis(β-hydroxyethyl)-N,N'-bis (4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis (β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine, 1,8-bis(2,5-diaminophenoxy)-3,6-dioxaoctane, their addition salts with an acid and their solvates.

Among the para-aminophenols, mention may for example be made of para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethyl phenol, 4-amino-2-aminomethylphenol, 4-amino-2-(β-hydroxyethylaminomethyl)phenol and 4-amino-2-fluorophenol, their addition salts with an acid and their solvates.

Among the ortho-aminophenols, examples that may be mentioned include 2-aminophenol, 2-amino-5-methylphenol, 2-amino-6-methylphenol and 5-acetamido-2-aminophenol, their addition salts with an acid and their solvates.

Among the heterocyclic bases, examples that may be mentioned include pyridine derivatives, pyrimidine derivatives and pyrazole derivatives.

Among the pyridine derivatives, mention may be made of the compounds described, for example, in patents GB 1 026 978 and GB 1 153 196, such as 2,5-diaminopyridine, 2-(4-methoxyphenyl)amino-3-aminopyridine, 3,4-diaminopyridine, their addition salts with an acid and their solvates.

Among the pyrimidine derivatives, mention may be made of the compounds described, for example, in patents DE 2 359 399; JP 88-169 571; JP 05-63124; EP 0 770 375 or patent application WO 96/15765, for instance 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in patent application FR-A-2 750 048, and among which mention may be made of pyrazolo[1,5-a]pyrimidine-3,7-diamine, 2,5-dimethylpyrazolo[1,5-a]pyrimidine-3,7-diamine, pyrazolo[1,5-a]pyrimidine-3,5-diamine, 2,7-dimethylpyrazolo [1,5-a]pyrimidine-3,5-diamine, 3-aminopyrazolo[1,5-a]pyrimidin-7-ol, 3-aminopyrazolo[1,5-a]pyrimidin-5-ol, 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl) amino]ethanol, 2-[(7-aminopyrazolo[1,5-a]pyrimidin-3-yl) (2-hydroxyethyl)amino]ethanol, 5,6-dimethylpyrazolo[1,5-a]pyrimidine-3,7-diamine, 2,6-dimethylpyrazolo[1,5-a] pyrimidine-3,7-diamine, 2,5-N7,N7-tetramethylpyrazolo[1,5-a]pyrimidine-3,7-diamine and 3-amino-5-methyl-7-imidazolylpropylaminopyrazolo[1,5-a]pyrimidine, their addition salts and their solvates.

Among the pyrazole derivatives, mention may be made of diaminopyrazole bases, especially the compounds described in patents DE 3843892 and DE 4133957 and patent applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-di amino-3-tert-butyl-1-methyl pyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the corresponding addition salts. It is also possible to use 4,5-diamino-1-(β-methoxyethyl)pyrazole, the addition salts thereof and the solvates thereof.

The addition salts of the oxidation bases present in the composition according to the invention are chosen especially from the addition salts with an acid, such as the hydrochlorides, hydrobromides, sulfates, citrates, succinates, tartrates, lactates, tosylates, benzenesulfonates, methanesulfonates, phosphates and acetates, and the addition salts with a base such as sodium hydroxide, potassium hydroxide, aqueous ammonia, amines or alkanolamines.

Moreover, the solvates of the additional oxidation bases more particularly represent the hydrates of said oxidation bases and/or the combination of said oxidation bases with a linear or branched $C_1$ to $C_4$ alcohol such as methanol, ethanol, isopropanol or n-propanol. Preferably, the solvates are hydrates.

In a particular embodiment, the composition according to the invention is free from oxidation bases chosen from para-phenylenediamine, para-toluenediamine, their addition salts, their solvates and the solvates of their salts.

When the composition according to the invention comprises one or more additional oxidation bases, the total content of the additional oxidation base(s), different from 2-(methoxymethyl)benzene-1,4-diamine of formula (I), its addition salts, its solvates and the solvates of its salts, present in the composition according to the invention, preferably ranges from 0.001% to 20% by weight, more preferentially from 0.005% to 15% by weight, better still from 0.01% to 10% by weight, even better still from 0.05% to 5% by weight, better yet from 0.1% to 3% by weight, relative to the total weight of the composition.

Couplers

The composition according to the invention comprises at least two particular couplers.

The composition according to the present invention comprises at least one coupler chosen from: 6-hydroxybenzomorpholine of formula (II), its addition salts, its solvates and/or the solvates of its salts, and mixtures thereof, and at least one coupler chosen from: 2-amino-5-ethoxyphenol of formula (III), its addition salts, its solvates and/or the solvates of its salts, and mixtures thereof.

(II)

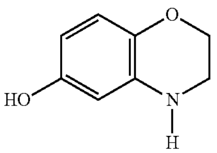

-continued (III)

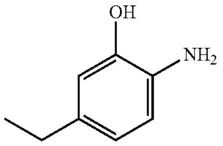

The addition salts of the compounds of formulae (II) and (III) are in particular chosen from addition salts with an acid such as hydrochlorides, hydrobromides, sulfates, citrates, succinates, tartrates, lactates, tosylates, benzenesulfonates, phosphates and acetates, and addition salts with a base such as sodium hydroxide, potassium hydroxide, aqueous ammonia, amines or alkanolamines.

Moreover, the solvates of the compounds of formulae (II) and (III) more particularly represent the hydrates of these compounds and/or the combination of these compounds with a linear or branched C1 to C4 alcohol such as methanol, ethanol, isopropanol or n-propanol. Preferably, the solvates are hydrates.

The total content of couplers chosen from the couplers of formulae (II) and (III), and also their addition salts, their solvates and/or the solvates of their salts, preferably ranges from 0.001% to 20% by weight, more preferentially from 0.005% to 15% by weight, better still from 0.01% to 10% by weight, even better still from 0.05% to 5% by weight, better yet from to 3% by weight, relative to the total weight of the composition.

The total content of couplers chosen from the couplers of formula (II), and also their addition salts, their solvates and/or the solvates of their salts, preferably ranges from 0.001% to 20% by weight, more preferentially from 0.005% to 15% by weight, better still from 0.01% to 10% by weight, even better still from 0.05% to 5% by weight, better yet from 0.1% to 3% by weight, relative to the total weight of the composition.

The total content of couplers chosen from the couplers of formula (III), and also their addition salts, their solvates and/or the solvates of their salts, preferably ranges from 0.001% to 20% by weight, more preferentially from 0.005% to 15% by weight, better still from 0.01% to 10% by weight, even better still from 0.05% to 5% by weight, better yet from 0.1% to 3% by weight, relative to the total weight of the composition.

The composition according to the invention may optionally also comprise one or more additional couplers, different from the compounds of formulae (II) and (III) and their addition salts, their solvates and/or the solvates of their salts, advantageously chosen from those traditionally used in the dyeing of keratin fibres.

Among the additional couplers, mention may in particular be made of meta-phenylenediamines, meta-aminophenols, meta-diphenols, naphthalene-based coupling agents and heterocyclic coupling agents, and the corresponding addition salts.

Mention may for example be made of 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethyl amino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 3,5-diamino-2,6-dimethoxypyridine, 2,6-bis (β-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b][1,2,4]triazole, 2,6-dimethyl[3,2-c][1,2,4]triazole and 6-methyl pyrazolo[1,5-a]benzimidazole, 2-methyl-5-aminophenol, 5-N-(β-hydroxyethyl)amino-2-methylphenol, 3-aminophenol, 3-amino-2-chloro-6-methylphenol, the corresponding addition salts with an acid and the corresponding mixtures.

In general, the addition salts of the couplers that may be used in the context of the invention are chosen in particular from the addition salts with an acid such as the hydrochlorides, hydrobromides, sulfates, citrates, succinates, tartrates, lactates, tosylates, benzenesulfonates, phosphates and acetates.

In a particular embodiment, the composition according to the invention is free from oxidation couplers chosen from resorcinol, 2-methylresorcinol, 4-chlororesorcinol, their addition salts, their solvates and the solvates of their salts.

When the composition comprises one or more additional oxidation couplers, the total content of the additional coupler(s), different from the couplers of formulae (II) and (III), their salts, their solvates and the solvates of their salts, present in the composition according to the invention preferably ranges from 0.001% to 20% by weight, more preferentially from 0.005% to 15% by weight, better still from 0.01% to 10% by weight, even better still from 0.05% to 5% by weight, better yet from 0.1% to 3% by weight, relative to the total weight of the composition.

Fatty Substance

The composition according to the invention may comprise one or more fatty substances.

Preferably, the composition according to the invention comprises one or more fatty substances.

Useful fatty substances according to the invention may be liquid fatty substances (or oils) and/or solid fatty substances. A liquid fatty substance is understood to be a fatty substance having a melting point of less than or equal to 25° C. at atmospheric pressure ($1.013\times10^5$ Pa) and a solid fatty substance is understood to be a fatty substance having a melting point of greater than 25° C. at atmospheric pressure ($1.013\times10^5$ Pa).

For the purposes of the present invention, the melting point corresponds to the temperature of the most endothermic peak observed on thermal analysis (differential scanning calorimetry or DSC) as described in the standard ISO 11357-3; 1999. The melting point may be measured using a differential scanning calorimeter (DSC), for example the calorimeter sold under the name MDSC 2920 by the company TA Instruments. In the present patent application, all the melting points are determined at atmospheric pressure ($1.013\times10^5$ Pa).

The term "fatty substance" is understood to mean an organic compound that is insoluble in water at 25° C. and at atmospheric pressure ($1.013\times10^5$ Pa) (solubility of less than 5% by weight, and preferably less than 1% by weight, even more preferentially less than 0.1% by weight). They bear in their structure at least one hydrocarbon-based chain including at least 6 carbon atoms and/or a sequence of at least two siloxane groups. In addition, the fatty substances are generally soluble in organic solvents under the same temperature and pressure conditions, for instance chloroform, dichloromethane, carbon tetrachloride, ethanol, benzene, toluene, tetrahydrofuran (THF), liquid petroleum jelly or decamethylcyclopentasiloxane.

Advantageously, the fatty substances that may be used in the present invention are neither (poly)oxyalkylenated nor (poly)glycerolated.

The term "non-silicone fatty substance" is intended to mean a fatty substance not containing any Si—O bonds and the term "silicone fatty substance" is intended to mean a fatty substance containing at least one Si—O bond.

Preferably, useful fatty substances according to the invention are non-silicone.

More particularly, the liquid fatty substance(s) according to the invention is/are chosen from C6 to C16 liquid hydrocarbons, liquid hydrocarbons comprising more than 16 carbon atoms, non-silicone oils of animal origin, oils of triglyceride type of plant or synthetic origin, fluoro oils, liquid fatty alcohols, liquid esters of fatty acid and/or of fatty alcohol other than triglycerides, and silicone oils, and mixtures thereof.

It is recalled that the fatty alcohols, esters and acids more particularly contain at least one saturated or unsaturated, linear or branched hydrocarbon-based group, comprising from 6 to 40 and better still from 8 to 30 carbon atoms, which is optionally substituted, in particular, with one or more hydroxyl groups (in particular 1 to 4). If they are unsaturated, these compounds may comprise one to three conjugated or unconjugated carbon-carbon double bonds.

As regards the C6 to C16 liquid hydrocarbons, these may be linear, branched, or optionally cyclic, and are preferably chosen from alkanes. Examples that may be mentioned include hexane, cyclohexane, undecane, dodecane, isododecane, tridecane or isoparaffins, such as isohexadecane or isodecane, and mixtures thereof.

The liquid hydrocarbons comprising more than 16 carbon atoms may be linear or branched, and of mineral or synthetic origin, and are preferably chosen from liquid paraffins or liquid petroleum jelly (or mineral oil), polydecenes, hydrogenated polyisobutene such as Parleam®, and mixtures thereof.

A hydrocarbon-based oil of animal origin that may be mentioned is perhydrosqualene.

The triglyceride oils of plant or synthetic origin are preferably chosen from liquid triglycerides of fatty acids comprising from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, castor oil, avocado oil, caprylic/capric acid triglycerides, for instance those sold by the company Stearinerie Dubois or those sold under the names Miglyol® 810, 812 and 818 by the company Dynamit Nobel, jojoba oil and shea butter oil, and mixtures thereof.

As regards the fluoro oils, they may be chosen from perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name Foralkyl® by the company Atochem; nonafluoromethoxybutane and nonafluoroethoxyisobutane; perfluoromorpholine derivatives such as 4-trifluoromethylperfluoromorpholine sold under the name PF 5052® by the company 3M.

The liquid fatty alcohols that are suitable for use in the invention are more particularly chosen from linear or branched, saturated or unsaturated alcohols, preferably unsaturated or branched alcohols, comprising from 6 to 40 carbon atoms, preferably from 8 to 30 carbon atoms.

Examples that may be mentioned include octyldodecanol, 2-butyloctanol, 2-hexyldecanol, 2-undecylpentadecanol, isostearyl alcohol, oleyl alcohol, linolenyl alcohol, ricinoleyl alcohol, undecylenyl alcohol and linoleyl alcohol, and mixtures thereof.

As regards the liquid esters of fatty acids and/or of fatty alcohols, other than the triglycerides mentioned previously, mention may be made especially of esters of saturated or unsaturated, linear C1 to C26 or branched C3 to C26 aliphatic mono- or polyacids and of saturated or unsaturated, linear C1 to C26 or branched C3 to C26 aliphatic mono- or polyalcohols, the total carbon number of the esters being greater than or equal to 6 and more advantageously greater than or equal to 10.

Preferably, for the esters of monoalcohols, at least one from among the alcohol and the acid from which the esters of the invention are derived is branched.

Among the monoesters, mention may be made of dihydroabietyl behenate; octyldodecyl behenate; isocetyl behenate; isostearyl lactate; lauryl lactate; linoleyl lactate; oleyl lactate; isostearyl octanoate; isocetyl octanoate; octyl octanoate; decyl oleate; isocetyl isostearate; isocetyl laurate; isocetyl stearate; isodecyl octanoate; isodecyl oleate; isononyl isononanoate; isostearyl palmitate; methyl acetyl ricinoleate; octyl isononanoate; 2-ethylhexyl isononanoate; octyldodecyl erucate; oleyl erucate; ethyl palmitate, isopropyl palmitate, such as 2-ethylhexyl palmitate, 2-octyldecyl palmitate; alkyl myristates such as isopropyl 2-octyldodecyl myristate, isobutyl stearate; 2-hexyldecyl laurate, and mixtures thereof.

Preferably, among the monoesters of monoacids and of monoalcohols, use will be made of ethyl palmitate and isopropyl palmitate, alkyl myristates such as isopropyl myristate or ethyl myristate, isocetyl stearate, 2-ethylhexyl isononanoate, isodecyl neopentanoate and isostearyl neopentanoate, and mixtures thereof.

Still within the context of this variant, esters of C4 to C22 dicarboxylic or tricarboxylic acids and of C1 to C22 alcohols and esters of monocarboxylic, dicarboxylic or tricarboxylic acids and of C2 to C26 dihydroxy, trihydroxy, tetrahydroxy or pentahydroxy alcohols may also be used.

Mention may notably be made of: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates, and mixtures thereof.

The composition may also comprise, as fatty ester, sugar esters and diesters of C6 to C30 and preferably C12 to C22 fatty acids. It is recalled that the term "sugar" refers to oxygen-bearing hydrocarbon-based compounds bearing several alcohol functions, with or without aldehyde or ketone functions, and which include at least 4 carbon atoms. These sugars may be monosaccharides, oligosaccharides or polysaccharides.

Examples of suitable sugars that may be mentioned include sucrose, glucose, galactose, ribose, fucose, maltose, fructose, mannose, arabinose, xylose and lactose, and derivatives thereof, especially alkyl derivatives, such as methyl derivatives, for instance methylglucose.

The sugar esters of fatty acids may be chosen especially from the group comprising the esters or mixtures of esters of sugars described previously and of linear or branched, saturated or unsaturated C6 to C30 and preferably C12 to C22 fatty acids. If they are unsaturated, these compounds may comprise one to three conjugated or unconjugated carbon-carbon double bonds.

The esters according to this variant may also be chosen from mono-, di-, tri- and tetraesters, polyesters, and mixtures thereof.

These esters may be, for example, oleates, laurates, palmitates, myristates, behenates, cocoates, stearates, linoleates, linolenates, caprates, arachidonates or mixtures thereof, for instance especially the mixed oleopalmitate, oleostearate and palmitostearate esters.

More particularly, use is made of monoesters and diesters and especially sucrose, glucose or methylglucose mono- or dioleates, -stearates, -behenates, -oleopalmitates, -linoleates, -linolenates and -oleostearates, and mixtures thereof.

An example that may be mentioned is the product sold under the name Glucate® DO by the company Amerchol, which is a methylglucose dioleate.

Preferably, use will be made of a liquid ester of a monoacid and of a monoalcohol.

The silicone oils that may be used in the composition A according to the present invention may be volatile or non-volatile, cyclic, linear or branched silicone oils, which are unmodified or modified with organic groups, and preferably have a viscosity from $5\times10^{-6}$ to 2.5 $m^2/s$ at 25° C., and preferably $1\times10^{-5}$ to 1 $m^2/s$.

Preferably, the silicone oils are chosen from polydialkylsiloxanes, especially polydimethylsiloxanes (PDMS), and liquid polyorganosiloxanes including at least one aryl group.

These silicone oils may also be organomodified. The organomodified silicone oils that may be used in accordance with the invention are preferably liquid silicones as defined previously and including in their structure one or more organofunctional groups attached via a hydrocarbon-based group, chosen, for example, from amine groups and alkoxy groups.

Organopolysiloxanes are defined in greater detail in Walter Noll's "Chemistry and Technology of Silicones" (1968), Academic Press. They may be volatile or non-volatile.

When they are volatile, the silicone oils are more particularly chosen from those with a boiling point of between 60° C. and 260° C., and even more particularly from:

(i) cyclic polydialkylsiloxanes including from 3 to 7 and preferably from 4 to 5 silicon atoms. These are, for example, octamethylcyclotetrasiloxane sold notably under the name Volatile Silicone® 7207 by Union Carbide or Silbione® 70045 V2 by Rhodia, decamethylcyclopentasiloxane sold under the name Volatile Silicone® 7158 by Union Carbide, and Silbione® 70045 V5 by Rhodia, and mixtures thereof.

Mention may also be made of cyclocopolymers of the dimethylsiloxane/methylalkylsiloxane type, such as Volatile Silicone® FZ 3109 sold by the company Union Carbide.

Mention may also be made of mixtures of cyclic polydialkylsiloxanes with organosilicon compounds, such as the mixture of octamethylcyclotetrasiloxane and tetra(trimethylsilyl)pentaerythritol (50/50) and the mixture of octamethylcyclotetrasiloxane and oxy-1,1'-bis(2,2,2',2',3,3'-hexatrimethylsilyloxy)neopentane;

(ii) linear volatile polydialkylsiloxanes containing 2 to 9 silicon atoms and having a viscosity of less than or equal to $5\times10^{-6}$ $m^2/s$ at 25° C. An example is decamethyltetrasiloxane sold in particular under the name SH 200 by Toray Silicone. Silicones falling within this category are also described in the article published in Cosmetics and Toiletries, Vol. 91, January 76, pp. 27-32, Todd & Byers, “Volatile Silicone Fluids for Cosmetics”.

Non-volatile polydialkylsiloxanes are preferably used.

These silicone oils are more particularly chosen from polydialkylsiloxanes, among which mention may be made mainly of polydimethylsiloxanes bearing trimethylsilyl end groups.

The viscosity of the silicones is measured at 25° C. according to the standard ASTM 445, Appendix C.

Among these polydialkylsiloxanes, mention may be made, in a nonlimiting manner, of the following commercial products:

- the Silbione® oils of the 47 and 70 047 series or the Mirasil® oils sold by Rhodia, such as, for example, the oil 70 047 V 500 000;
- the oils of the Mirasil® series sold by the company Rhodia;
- the oils of the 200 series from Dow Corning, such as DC200 having a viscosity of 60 000 $mm^2/s$;
- the Viscasil® oils from General Electric and certain oils of the SF series (SF 96, SF 18) from General Electric.

Mention may also be made of polydimethylsiloxanes bearing dimethylsilanol end groups, known under the name dimethiconol (CTFA), such as the oils of the 48 series from the company Rhodia.

The organomodified silicones that may be used in accordance with the invention are silicones as defined previously and comprising in their structure one or more organofunctional groups attached via a hydrocarbon-based group.

As regards the liquid polyorganosiloxanes including at least one aryl group, they may especially be polydiphenylsiloxanes, and polyalkylarylsiloxanes functionalized with the organofunctional groups mentioned previously.

The polyalkylarylsiloxanes are particularly chosen from linear and/or branched polydimethyl/methylphenylsiloxanes and polydimethyl/diphenylsiloxanes with a viscosity ranging from $1\times10^{-5}$ to $5\times10^{-2}$ $m^2/s$ at 25° C.

Among these polyalkylarylsiloxanes, examples that may be mentioned include the products sold under the following names:

- the Silbione® oils of the 70 641 series from Rhodia;
- the oils of the Rhodorsil® 70 633 and 763 series from Rhodia;
- the oil Dow Corning 556 Cosmetic Grade Fluid from Dow Corning;
- the silicones of the PK series from Bayer, such as the product PK20;
- the silicones of the PN and PH series from Bayer, such as the products PN1000 and PH1000;
- certain oils of the SF series from General Electric, such as SF 1023, SF 1154, SF 1250 and SF 1265.

Among the organomodified silicones, mention may be made of polyorganosiloxanes including:

- substituted or unsubstituted amine groups, such as the products sold under the names GP 4 Silicone Fluid and GP 7100 by the company Genesee or the products sold under the names Q2 8220 and Dow Corning 929 or 939 by the company Dow Corning. The substituted amine groups are in particular C1 to C4 aminoalkyl groups;
- alkoxy groups,
- hydroxyl groups.

The solid fatty substances according to the invention preferably have a viscosity of greater than 2 Pa·s, measured at 25° C. and at a shear rate of 1 $s^{-1}$.

The solid fatty substance(s) is/are preferably chosen from solid fatty acids, solid fatty alcohols, solid esters of fatty acids and/or of fatty alcohols, waxes, ceramides and mixtures thereof.

The term “fatty acids” is intended to mean a long-chain carboxylic acid comprising from 6 to 40 carbon atoms, preferably from 8 to 30 carbon atoms. The solid fatty acids according to the invention preferentially comprise from 10 to 30 carbon atoms and better still from 14 to 22 carbon atoms. They may optionally be hydroxylated. These fatty acids are neither oxyalkylenated nor glycerolated.

The solid fatty acids that may be used in the present invention are especially chosen from myristic acid, cetylic acid, stearylic acid, palmitic acid, arachidic acid, stearic acid, lauric acid, behenic acid, 12-hydroxystearic acid, and mixtures thereof.

Particularly preferably, the fatty acid(s) is/are chosen from behenic acid and arachidic acid.

The term “fatty alcohol” is intended to mean a long-chain aliphatic alcohol comprising from 6 to 40 carbon atoms, preferably from 8 to 30 carbon atoms, and comprising at least one hydroxyl group OH. These fatty alcohols are neither oxyalkylenated nor glycerolated.

The solid fatty alcohols may be saturated or unsaturated, and linear or branched, and include from 8 to 40 carbon atoms, preferably from 10 to 30 carbon atoms. Preferably, the solid fatty alcohols have the structure R—OH with R denoting a linear alkyl group, optionally substituted with one or more hydroxyl groups, comprising from 8 to 40, preferentially from to 30 carbon atoms, better still from 10 to 30, or even from 12 to 24 and even better still from 14 to 22 carbon atoms.

The solid fatty alcohols that may be used are preferably chosen from saturated or unsaturated, linear or branched, preferably linear and saturated, (mono)alcohols including from 8 to 40 carbon atoms, better still from 10 to 30, or even from 12 to 24 and even better still from 14 to 22 carbon atoms.

The solid fatty alcohols that may be used may be chosen, alone or as a mixture, from: myristyl alcohol (or 1-tetradecanol); cetyl alcohol (or 1-hexadecanol); stearyl alcohol (or 1-octadecanol); arachidyl alcohol (or 1-eicosanol); behenyl alcohol (or 1-docosanol); lignoceryl alcohol (or 1-tetracosanol); ceryl alcohol (or 1-hexacosanol); montanyl alcohol (or 1-octacosanol); myricyl alcohol (or 1-triacontanol).

Preferentially, the solid fatty alcohol is chosen from cetyl alcohol, stearyl alcohol, behenyl alcohol, myristyl alcohol, arachidyl alcohol, and mixtures thereof, such as cetylstearyl alcohol or cetearyl alcohol. Particularly preferably, the solid fatty alcohol is behenyl alcohol.

The solid esters of a fatty acid and/or of a fatty alcohol that may be used are preferably chosen from esters derived from a C9-C26 carboxylic fatty acid and/or from a C9-C26 fatty alcohol.

Preferably, these solid fatty esters are esters of a linear or branched, saturated carboxylic acid including at least 10 carbon atoms, preferably from 10 to 30 carbon atoms and more particularly from 12 to 24 carbon atoms, and of a linear or branched, saturated monoalcohol, including at least 10 carbon atoms, preferably from 10 to 30 carbon atoms and more particularly from 12 to 24 carbon atoms. The saturated carboxylic acids may be optionally hydroxylated, and are preferably monocarboxylic acids.

Esters of C4-C22 dicarboxylic or tricarboxylic acids and of C1-C22 alcohols and esters of monocarboxylic, dicarboxylic or tricarboxylic acids and of C2-C26 dihydroxylated, trihydroxylated, tetrahydroxylated or pentahydroxylated alcohols may also be used.

Mention may in particular be made of octyldodecyl behenate, isocetyl behenate, cetyl lactate, stearyl octanoate, octyl octanoate, cetyl octanoate, decyl oleate, hexyl stearate, octyl stearate, myristyl stearate, cetyl stearate, stearyl stearate, octyl pelargonate, cetyl myristate, myristyl myristate, stearyl myristate, diethyl sebacate, diisopropyl sebacate, diisopropyl adipate, di-n-propyl adipate, dioctyl adipate, dioctyl maleate, octyl palmitate, myristyl palmitate, cetyl palmitate, stearyl palmitate, and mixtures thereof.

Preferably, the solid esters of a fatty acid and/or of a fatty alcohol are chosen from C9-C26 alkyl palmitates, notably myristyl palmitate, cetyl palmitate or stearyl palmitate; C9-C26 alkyl myristates, such as cetyl myristate, stearyl myristate and myristyl myristate; and C9-C26 alkyl stearates, notably myristyl stearate, cetyl stearate and stearyl stearate; and mixtures thereof.

For the purposes of the present invention, a wax is a lipophilic compound, which is solid at and atmospheric pressure, with a reversible solid/liquid change of state, having a melting point greater than about 40° C., which may range up to 200° C., and having in the solid state an anisotropic crystal organization. In general, the size of the wax crystals is such that the crystals diffract and/or scatter light, giving the composition that comprises them a more or less opaque cloudy appearance. By bringing the wax to its melting point, it is possible to make it miscible with oils and to form a microscopically homogeneous mixture, but on returning the temperature of the mixture to ambient temperature, recrystallization of the wax, which is microscopically and macroscopically detectable (opalescence), is obtained.

In particular, the waxes that are suitable for use in the invention may be chosen from waxes of animal, plant or mineral origin, non-silicone synthetic waxes, and mixtures thereof.

Mention may be made notably of hydrocarbon-based waxes, for instance beeswax, notably of biological origin, lanolin wax and Chinese insect waxes; rice bran wax, carnauba wax, candelilla wax, ouricury wax, esparto grass wax, berry wax, shellac wax, Japan wax and sumac wax; montan wax, orange wax and lemon wax, microcrystalline waxes, paraffins and ozokerite; polyethylene waxes, the waxes obtained by Fischer-Tropsch synthesis and waxy copolymers, and also esters thereof.

Mention may additionally be made of C20 to C60 microcrystalline waxes, such as Microwax HW.

Mention may also be made of the MW 500 polyethylene wax sold under the reference Permalen 50-L polyethylene.

Mention may also be made of the waxes obtained by catalytic hydrogenation of animal or plant oils containing linear or branched C8-C32 fatty chains. Among these waxes mention may especially be made of isomerized jojoba oil such as the trans-isomerized partially hydrogenated jojoba oil, especially the product manufactured or sold by the company Desert Whale under the commercial reference Iso-Jojoba-50®, hydrogenated sunflower oil, hydrogenated castor oil, hydrogenated coconut oil, hydrogenated lanolin oil and bis(1,1,1-trimethylolpropane) tetrastearate, especially the product sold under the name Hest 2T-4S® by the company Heterene.

The waxes obtained by hydrogenation of castor oil esterified with cetyl alcohol, such as those sold under the names Phytowax Castor 16L64® and 22L73® by the company Sophim, may also be used.

A wax that may also be used is a C20-C40 alkyl (hydroxystearyloxy)stearate (the alkyl group containing from 20 to 40 carbon atoms), alone or as a mixture. Such a wax is especially sold under the names Kester Wax K 82 P®, Hydroxypolyester K 82 PC, and Kester Wax K 80 P®, by the company Koster Keunen.

It is also possible to use microwaxes in the compositions of the invention; mention may be made especially of carnauba microwaxes, such as the product sold under the name MicroCare 350® by the company Micro Powders, synthetic-wax microwaxes, such as the product sold under the name MicroEase 114S® by the company Micro Powders, microwaxes constituted of a mixture of carnauba wax and polyethylene wax, such as the products sold under the names Micro Care 300® and 310® by the company Micro Powders, microwaxes constituted of a mixture of carnauba wax and of synthetic wax, such as the product sold under the name Micro Care 325® by the company Micro Powders, polyethylene microwaxes, such as the products sold under the names Micropoly 200®, 220®, 220L® and 250S® by the company Micro Powders, and polytetrafluoroethylene microwaxes, such as the products sold under the names Microslip 519® and 519 L® by the company Micro Powders.

The waxes are preferably chosen from mineral waxes, for instance paraffin, petroleum jelly, lignite or ozokerite wax; plant waxes, for instance cocoa butter or cork fibre or sugar cane waxes, olive tree wax, rice wax, hydrogenated jojoba wax, ouricury wax, carnauba wax, candelilla wax, esparto grass wax, or absolute waxes of flowers, such as the essential wax of blackcurrant blossom sold by the company Bertin (France); waxes of animal origin, for instance beeswaxes or modified beeswaxes (cera bellina), spermaceti, lanolin wax and lanolin derivatives; microcrystalline waxes; and mixtures thereof.

The ceramides, or ceramide analogues such as glycoceramides, which may be used in the compositions according to the invention, are known; mention may in particular be made of ceramides of classes I, II, III and V according to the Dawning classification.

The ceramides or analogues thereof that may be used preferably correspond to the following formula: $R^3CH(OH)CH(CH_2OR^2)(NHCOR^1)$, in which:

- $R^1$ denotes a linear or branched, saturated or unsaturated alkyl group, derived from $C_{14}$-$C_{30}$ fatty acids, it being possible for this group to be substituted with a hydroxyl group in the alpha position, or a hydroxyl group in the omega position esterified with a saturated or unsaturated $C_{16}$-$C_{30}$ fatty acid;
- $R^2$ denotes a hydrogen atom, a (glycosyl)n group, a (galactosyl)m group or a sulfogalactosyl group, in which n is an integer ranging from 1 to 4 and m is an integer ranging from 1 to 8;
- $R^3$ denotes a $C_{15}$-$C_{26}$ hydrocarbon-based group, saturated or unsaturated in the alpha position, it being possible for this group to be substituted with one or more $C_1$-$C_{14}$ alkyl groups; it being understood that in the case of natural ceramides or glycoceramides, $R^3$ may also denote a $C_{15}$-$C_{26}$ alpha-hydroxyalkyl group, the hydroxyl group being optionally esterified by a C16-$C_{30}$ alpha-hydroxy acid.

The ceramides that are more particularly preferred are the compounds for which $R^1$ denotes a saturated or unsaturated alkyl derived from $C_{16}$-$C_{22}$ fatty acids; $R^2$ denotes a hydrogen atom and $R^3$ denotes a saturated linear $C_{15}$ group.

Preferentially, use is made of ceramides for which $R^1$ denotes a saturated or unsaturated alkyl group derived from $C_{14}$-$C_{30}$ fatty acids; $R^2$ denotes a galactosyl or sulfogalactosyl group; and $R^3$ denotes a —CH═CH—(CH2)$_{12}$—CH3 group.

Use may also be made of the compounds for which $R^1$ denotes a saturated or unsaturated alkyl radical derived from $C_{12}$-$C_{22}$ fatty acids; $R^2$ denotes a galactosyl or sulfogalactosyl radical and $R^3$ denotes a saturated or unsaturated $C_{12}$-$C_{22}$ hydrocarbon-based radical and preferably a —CH═CH—(CH2)$_{12}$—CH3 group.

As compounds that are particularly preferred, mention may also be made of 2-N-linoleoylaminooctadecane-1,3-diol; 2-N-oleoylaminooctadecane-1,3-diol; 2-N-palmitoylaminooctadecane-1,3-diol; 2-N-stearoylaminooctadecane-1,3-diol; 2-N-behenoylaminooctadecane-1,3-diol; 2-N-[2-hydroxypaimitoyl]aminooctadecane-1,3-diol; 2-N-stearoylaminooctadecane-1,3,4-triol and in particular N-stearoylphytosphingosine, 2-N-palmitoylaminohexadecane-1,3-diol, N-linoleoyldihydrosphingosine, N-oleoyldihydrosphingosine, N-palmitoyldihydrosphingosine, N-stearoyldihydrosphingosine, and N-behenoyldlhydrosphingosine, N-docosanoyl-N-methyl-D-glucamine, cetylic acid N-(2-hydroxyethyl)-N-(3-cetyloxy-2-hydroxypropyl)amide and bis(N-hydroxyethyl-N-cetyl)malonamide; and mixtures thereof. N-Oleoyldihydrosphingosine will preferably be used.

The solid fatty substances are preferably chosen from solid fatty acids, solid fatty alcohols and mixtures thereof.

According to a preferred embodiment, useful fatty substances according to the invention are chosen from liquid fatty substances, more preferentially from liquid hydrocarbons containing more than 16 carbon atoms, plant oils, liquid fatty alcohols and liquid fatty esters, silicone oils and mixtures thereof.

Preferentially, the liquid fatty substance(s) is/are chosen from liquid hydrocarbons comprising more than 16 carbon atoms, in particular liquid petroleum jelly, liquid fatty alcohols, and mixtures thereof.

According to another particular embodiment, the fatty substances that are useful according to the invention are chosen from solid fatty substances, preferably from solid fatty alcohols.

According to another preferred embodiment, the composition according to the invention comprises at least one liquid fatty substance and at least one solid fatty substance, preferentially at least one liquid fatty alcohol and at least one solid fatty alcohol.

When the composition according to the invention comprises one or more fatty substances, the total content of the fatty substance(s) preferably ranges from 5% to 80% by weight, more preferentially from 8% to 70% by weight, and better still from 10% to 65% by weight, relative to the total weight of the composition.

In a particular embodiment, the composition according to the invention comprises one or more fatty substances, the total content of the fatty substance(s) preferably ranging from 30% to 80% by weight, more preferentially from 35% to 70% by weight, and better still from 40% to 65% by weight, relative to the total weight of the composition.

In another particular embodiment, the composition according to the invention comprises one or more liquid fatty substances, the total content of the liquid fatty substance(s) preferably ranging from 30% to 80% by weight, more preferentially from 35% to 70% by weight, and better still from 40% to 65% by weight, relative to the total weight of the composition.

Surfactants

The composition according to the present invention may comprise one or more surfactants. These may be chosen from anionic surfactants, nononic surfactants and cationic surfactants and/or mixtures thereof.

Preferably, the composition according to the present invention comprises one or more surfactants.

The term "anionic surfactant" is understood to mean a surfactant including, as ionic or ionizable groups, only anionic groups. These anionic groups are preferably chosen from the following groups: $CO_2H$, $CO_2^-$, $SO_3H$, $SO_3^-$, $OSO_3H$, $OSO_3^-$, $H_2PO_3$, $HPO_3^-$, $PO_3^{2-}$, $H_2PO_2$, $HPO_2^-$, $PO_2^{2-}$, POH and $PO^-$.

As examples of anionic surfactants that can be used in the composition according to the invention, mention may be made of alkyl sulfates, alkyl ether sulfates, alkylamido ether sulfates, alkylaryl polyether sulfates, monoglyceride sulfates, alkylsulfonates, alkylamidesulfonates, alkylaryisulfonates, α-olefinsulfonates, paraffin sulfonates, alkyl sulfosuccinates, alkyl ether sulfosuccinates, alkylamide sulfosuccinates, alkyl sulfoacetates, acyl sarcosinates, acyl glutamates, alkyl sulfosuccinamates, acyl isethionates and N—(C1-C4)alkyl N-acyltaurates, salts of alkyl monoesters of polyglycoside-polycarboxylic acids, acyl lactylates, salts of D-galactoside uronic acids, salts of alkyl ether carboxylic acids, salts of alkylaryl ether carboxylic acids, salts of alkylamido ether carboxylic acids; and the corresponding non-salified forms of all these compounds; the alkyl and acyl groups of all these compounds (unless specified otherwise) generally comprising from 6 to 24 carbon atoms and the aryl group generally denoting a phenyl group.

These compounds may be oxyethylenated and then preferably comprise from 1 to 50 ethylene oxide units.

The salts of $C_6$-$C_{24}$ alkyl monoesters of polyglycoside-polycarboxylic acids may be chosen from $C_6$-$C_{24}$ alkyl polyglycoside-citrates, $C_6$-$C_{24}$ alkyl polyglycoside-tartrates and $C_6$-$C_{24}$ alkyl polyglycoside-sulfosuccinates.

When the anionic surfactant(s) are in salt form, they may be chosen from alkali metal salts such as the sodium or potassium salt and preferably the sodium salt, ammonium salts, amine salts and in particular amino alcohol salts or alkaline-earth metal salts such as the magnesium salt.

Examples of amino alcohol salts that may notably be mentioned include monoethanolamine, diethanolamine and triethanolamine salts, monoisopropanolamine, dllsopropanolamine or trilsopropanolamine salts, 2-amino-2-methyl-1-propanol salts, 2-amino-2-methyl-1,3-propanediol salts and tris(hydroxymethyl)aminomethane salts.

Alkali metal or alkaline-earth metal salts and in particular the sodium or magnesium salts are preferably used.

The anionic surfactants optionally present may be mild anionic surfactants, i.e. anionic surfactants without a sulfate function.

As regards mild anionic surfactants, mention may be made in particular of the following compounds and salts thereof, and also mixtures thereof: polyoxyalkylenated alkyl ether carboxylic acids, polyoxyalkylenated alkylaryl ether carboxylic acids, polyoxyalkylenated alkylamido ether carboxylic acids, in particular those comprising 2 to 50 ethylene oxide groups, alkyl D-galactoside uronic acids, acyl sarcosinates, acyl glutamates and alkylpolyglycoside carboxylic esters.

Use may be made most particularly of polyoxyalkylenated alkyl ether carboxylic acids, for instance lauryl ether carboxylic acid (4.5 EO), sold, for example, under the name Akypo RLM 45 CA from Kao.

Among the anionic surfactants mentioned above, use is preferably made of sulfated surfactants such as alkyl sulfates or alkyl ether sulfates, and acyl glutamates, more preferentially sulfated anionic surfactants, even more preferentially alkyl sulfates.

The nononic surfactant(s) that may be used in the composition of the present invention are in particular described, for example, in the *Handbook of Surfactants* by M. R. Porter, published by Blackie & Son (Glasgow and London), 1991, pages 116-178.

Examples of nonionic surfactants that may be mentioned include the following compounds, alone or as a mixture:

oxyalkylenated ($C_8$-$C_{24}$)alkylphenols;

saturated or unsaturated, linear or branched, oxyalkylenated or glycerolated $C_8$-$C_{40}$ alcohols, preferably comprising one or two fatty chains;

saturated or unsaturated, linear or branched, oxyalkylenated $C_8$ to $C_{30}$ fatty acid amides;

esters of saturated or unsaturated, linear or branched, $C_8$ to $C_{30}$ acids and of polyethylene glycols;

esters of saturated or unsaturated, linear or branched, $C_8$ to $C_{30}$ acids and of sorbitol which are preferably oxyethylenated;

esters of fatty acids and of sucrose;

$C_8$-$C_{30}$ fatty acid esters of sorbitan, ($C_8$-$C_{30}$)alkyl(poly)glucosides, ($C_8$-$C_{30}$)alkenyl(poly) glucosides, which are optionally oxyalkylenated (0 to 10 oxyalkylene units) and comprising from 1 to 15 glucose units, ($C_8$-$C_{30}$)alkyl(poly)glucoside esters;

saturated or unsaturated oxyethylenated plant oils;

condensates of ethylene oxide and/or of propylene oxide;

N—($C_8$-$C_{30}$)alkylglucamine and N—($C_8$-$C_{30}$)acylmethylglucamine derivatives;

amine oxides.

They are notably chosen from alcohols, α-diols and ($C_1$-$C_{20}$)alkylphenols, these compounds being ethoxylated, propoxylated or glycerolated and bearing at least one fatty chain comprising, for example, from 8 to 24 carbon atoms, preferably from 8 to 18 carbon atoms, the number of ethylene oxide or propylene oxide groups possibly ranging notably from 1 to 200, and the number of glycerol groups possibly ranging notably from 1 to 30.

Mention may also be made of condensates of ethylene oxide and of propylene oxide with fatty alcohols, ethoxylated fatty amides preferably containing from 1 to 30 ethylene oxide units, polyglycerolated fatty amides comprising on average from 1 to 5, and in particular from 1.5 to 4, glycerol groups, ethoxylated fatty acid esters of sorbitan containing from 1 to 30 ethylene oxide units, fatty acid esters of sucrose, fatty acid esters of polyethylene glycol, ($C_8$-$C_{24}$ alkyl)polyglycosides, oxyethylenated plant oils, N—($C_6$-$C_{24}$ alkyl)glucamine derivatives, amine oxides such as ($C_{10}$-$C_{14}$ alkyl)amine oxides or N—($C_{10}$-$C_{14}$ acyl)aminopropylmorpholine oxides.

The $C_8$-$C_{30}$, preferably $C_{12}$-$C_{22}$, fatty acid esters (especially monoesters, diesters and triesters) of sorbitan may be chosen from:

sorbitan caprylate; sorbitan cocoate; sorbitan isostearate; sorbitan laurate; sorbitan oleate; sorbitan palmitate; sorbitan stearate; sorbitan diisostearate; sorbitan dioleate; sorbitan distearate; sorbitan sesquicaprylate; sorbitan sesquiisostearate; sorbitan sesquioleate; sorbitan sesquistearate; sorbitan triisostearate; sorbitan trioleate; sorbitan tristearate.

The polyoxyethylenated $C_8$-$C_{30}$ (preferably $C_{12}$-$C_{18}$) fatty acid esters (especially monoesters, diesters and triesters) of sorbitan especially containing from 2 to 20 mol of ethylene oxide may be chosen from polyoxyethylenated esters of $C_{12}$-$C_{18}$ fatty acids, in particular lauric, myristic, cetylic or stearic acid, and of sorbitan especially containing from 2 to 30 mol of ethylene oxide, such as:

polyoxyethylenated sorbitan monolaurate (4 EO) (POLYSORBATE-21), polyoxyethylenated sorbitan monolaurate (20 EO) (POLYSORBATE-20), polyoxyethylenated sorbitan monopalmitate (20 EO) (POLYSORBATE-40), polyoxyethylenated sorbitan monostearate (20 EO) (POLYSORBATE-60), polyoxyethylenated sorbitan monostearate (4 EO) (POLYSORBATE-61), polyoxyethylenated sorbitan monooleate (20 EO) (POLYSORBATE-80), polyoxyethylenated sorbitan monooleate (5 EO) (POLYSORBATE-81), polyoxyethylenated sorbitan tristearate (20 EO) (POLYSORBATE-65), polyoxyethylenated sorbitan trioleate (20 EO) (POLYSORBATE-85).

The polyoxyethylenated $C_8$-$C_{30}$ (preferably $C_{12}$-$C_{18}$) fatty acid esters (especially monoesters, diesters, triesters and tetraesters) of sorbitan, especially containing from 2 to 20 mol of ethylene oxide, may be chosen from polyoxyethylenated esters, especially containing from 2 to 20 mol of ethylene oxide of $C_{12}$-$C_{18}$ fatty acids, in particular lauric, myristic, cetylic or stearic acid, and of sorbitan, such as:

the ester polyoxyethylenated with 20 EO of sorbitan and of cocoic acid (PEG-20 Sorbitan Cocoate);

the polyoxyethylenated esters (especially containing from 2 to 20 EO) of sorbitan and of isostearic acid (such as PEG-2 Sorbitan Isostearate; PEG-5 Sorbitan Isostearate; PEG-20 Sorbitan Isostearate such as the product sold under the name Nikkol TI 10 V by the company Nikkol), the polyoxyethylenated esters (especially containing from 2 to 20 EO) of sorbitan and of lauric acid (such as PEG-10 Sorbitan Laurate), the polyoxyethylenated esters (especially containing from 2 to 20 EO) of sorbitan and of oleic acid containing 10 oxyethylene groups (such as PEG-6 Sorbitan Oleate; PEG-20 sorbitan oleate), the polyoxyethylenated esters (especially containing from 3 to 20 EO) of sorbitan and of stearic acid (such as PEG-3 Sorbitan Stearate; PEG-4 Sorbitan Stearate; PEG-6 Sorbitan Stearate).

The nonionic surfactant(s) is/are preferably chosen from ethoxylated $C_8$-$C_{24}$ fatty alcohols comprising from 1 to 200 ethylene oxide groups, ethoxylated $C_8$-$C_{30}$ fatty acid esters of sorbitan having from 1 to 30 ethylene oxide units, ($C_6$-$C_{24}$ alkyl)polyglycosides, and mixtures thereof, better still from ethoxylated $C_8$-$C_{24}$ fatty alcohols comprising from 1 to 200 ethylene oxide groups, ($C_6$-$C_{24}$ alkyl)polyglycosides, and mixtures thereof.

The cationic surfactant(s) that may be used in the composition according to the invention are generally chosen from optionally polyoxyalkylenated primary, secondary or tertiary fatty amines, quaternary ammonium salts, and mixtures thereof.

The fatty amines generally comprise at least one $C_8$-$C_{30}$ hydrocarbon-based chain. Among the fatty amines that may be used according to the invention, examples that may be mentioned include stearylamidopropylcimethylamine and distearylamine.

Examples of quaternary ammonium salts that may notably be mentioned include:

those corresponding to the general formula (X) below:

(X)

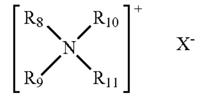

in which the groups $R_8$ to $R_{11}$, which may be identical or different, represent a linear or branched aliphatic group comprising from 1 to 30 carbon atoms, or an aromatic group such as aryl or alkylaryl, at least one of the groups $R_8$ to $R_{11}$ comprising from 8 to 30 carbon atoms and preferably from 12 to 24 carbon atoms. The aliphatic groups may include heteroatoms such as especially oxygen, nitrogen, sulfur and halogens.

The aliphatic groups are chosen, for example, from $C_1$-$C_{30}$ alkyl, $C_1$-$C_{30}$ alkoxy, polyoxy($C_2$-$C_6$)alkylene, $C_1$-$C_{30}$ alkylamide, ($C_{12}$-$C_{22}$)alkylamido($C_2$-$C_6$)alkyl, ($C_1$-$C_{22}$)alkyl acetate and $C_1$-$C_{30}$ hydroxyalkyl groups; $X^-$ is an anion chosen from the group of halides, phosphates, acetates, lactates, ($C_1$-$C_4$)alkyl sulfates and ($C_1$-$C_4$)alkylsulfonates or ($C_1$-$C_4$)alkylaryisulfonates.

Among the quaternary ammonium salts of formula (X), preference is given, firstly, to tetraalkylammonium chlorides, for instance dialkyldimethylammonium or alkyltrimethylammonium chlorides in which the alkyl group includes from about 12 to 22 carbon atoms, in particular behenyltrimethylammonium chloride, distearylcimethylammonium chloride, cetyltrimethylammonium chloride or benzydimethystearylammonium chloride, or, secondly, to distearoylethylhydroxyethylmethylammonium methosulfate, dipalmitoylethylhydroxyethylammonium methosulfate or distearoylethylhydroxyethylammonium methosulfate, or also, finally, to palmitylamldopropyltrimethylammonium chloride or stearamidopropyldimethyl(myristyl acetate)ammonium chloride, sold under the name Ceraphyl® 70 by the company Van Dyk;

quaternary ammonium salts of imidazoline, for instance those of formula (XI) below:

(XI)

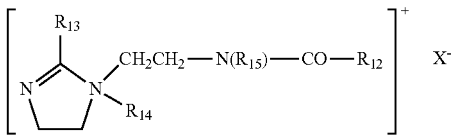

in which R12 represents an alkenyl or alkyl group including from 8 to 30 carbon atoms, for example tallow fatty acid derivatives, R13 represents a hydrogen atom, a $C_1$-$C_4$ alkyl group or an alkenyl or alkyl group including from 8 to 30 carbon atoms, R14 represents a $C_1$-$C_4$ alkyl group, R15 represents a hydrogen atom or a $C_1$-$C_4$ alkyl group, and $X^-$ is an anion chosen from the group of halides, phosphates, acetates, lactates, ($C_1$-$C_4$)alkyl sulfates, and ($C_1$-$C_4$)alkysulfonates or ($C_1$-$C_4$) alkylarylsulfonates.

Preferably, R12 and R13 denote a mixture of alkenyl or alkyl groups including from 12 to 21 carbon atoms, for example tallow fatty acid derivatives, R14 denotes a methyl group and R15 denotes a hydrogen atom. Such a product is sold, for example, under the name Rewoquat® W 75 by the company Rewo;

quaternary diammonium or triammonium salts, in particular of formula (XII) below:

(XII)

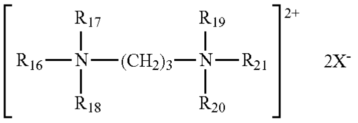

in which R16 denotes an alkyl group containing approximately from 16 to 30 carbon atoms, which is optionally hydroxylated and/or interrupted with one or more oxygen atoms; R17 is chosen from hydrogen, an alkyl group containing from 1 to 4 carbon atoms or a group —(CH2)3-N+(R16a)(R17a)(R18a), R16a, R17a, R18a, R18, R19, R20 and R21, which may be Identical or different, are chosen from hydrogen or an alkyl group containing from 1 to 4 carbon atoms, and X— is an anion chosen from the group of halides, acetates, phosphates, nitrates, (C1-C4)alkyl sulfates, (C1-C4)alkylsulfonates or (C1-C4)alkylarylsulfonates, in particular methyl sulfate and ethyl sulfate.

Such compounds are, for example, Finquat CT-P, sold by the company Finetex (Quaternium 89), and Finquat CT, sold by the company Finetex (Quaternium 75);

quaternary ammonium salts containing one or more ester functions, for instance those of formula (XIII) below:

(XIII)

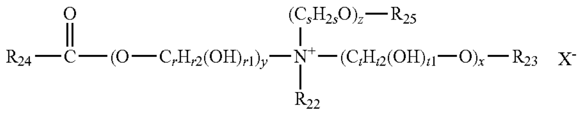

in which: R22 is chosen from C1-C6 alkyl groups and C1-C6 hydroxyalkyl or dihydroxyalkyl groups; R23 is chosen from: the group —C(O)R26, linear or branched, saturated or unsaturated C1-C22 hydrocarbon-based groups R27, or a hydrogen atom; R25 is chosen from: the group —C(O)R28, linear or branched, saturated or unsaturated C1-C6 hydrocarbon-based groups R29, or a hydrogen atom; R24, R26 and R28, which may be identical or different, are chosen from linear or branched, saturated or unsaturated C7-C21 hydrocarbon-based groups; r, s and t, which may be identical or different, are integers from 2 to 6; r1 and t1, which may be identical or different, are 0 or 1; r2+r1=2 r and t1+t2=2 t, y is an integer from 1 to 10, x and z, which may be identical or different, are integers from 0 to 10, X— is an organic or inorganic simple or complex anion, with the proviso that the sum x+y+z is from 1 to 15, that when x is 0 R23 denotes R27 and that when z is 0 R25 denotes R29.

The alkyl groups R22 may be linear or branched, and more particularly linear.

Preferably, R22 denotes a methyl, ethyl, hydroxyethyl or dihydroxypropyl group, and more particularly a methyl or ethyl group.

Advantageously, the sum x+y+z is from 1 to 10.

When R23 is a hydrocarbon-based group R27, it may be long and contain from 12 to 22 carbon atoms, or may be short and contain from 1 to 3 carbon atoms.

When R25 is a hydrocarbon-based group R29, it preferably contains 1 to 3 carbon atoms.

Advantageously, R24, R26 and R28, which may be Identical or different, are chosen from linear or branched, saturated or unsaturated C11-C21 hydrocarbon-based groups, and more particularly from linear or branched, saturated or unsaturated C11-C21 alkyl and alkenyl groups.

Preferably, x and z, which may be identical or different, are equal to 0 or 1.

Advantageously, y is equal to 1.

Preferably, r, s and t, which may be identical or different, are equal to 2 or 3, and even more particularly are equal to 2.

The anion $X^-$ is preferably a halide, preferably chloride, bromide or iodide, a (C1-C4)alkyl sulfate, (C1-C4)alkylsulfonate or (C1-C4)alkylarylsulfonate. However, use may be made of methanesulfonate, phosphate, nitrate, tosylate, an anion derived from an organic acid, such as acetate or lactate, or any other anion that is compatible with the ammonium bearing an ester function.

The anion $X^-$ is even more particularly chloride, methyl sulfate or ethyl sulfate.

Use is made more particularly, in the composition according to the invention, of the ammonium salts of formula (XIII) in which: R22 denotes a methyl or ethyl group, x and y are equal to 1, z is equal to 0 or 1, r, s and t are equal to 2; R23 is chosen from: the group —C(O)R26, methyl, ethyl or C14-C22 hydrocarbon-based groups, or a hydrogen atom, R25 is chosen from: the group —C(O)R28, or a hydrogen atom, R24, R26 and R28, which may be identical or different, are chosen from linear or branched, saturated or unsaturated C13-C17 hydrocarbon-based groups, and preferably from linear or branched, saturated or unsaturated C13-C17 alkyl and alkenyl groups.

Advantageously, the hydrocarbon-based groups are linear.

Among the compounds of formula (XIII), examples that may be mentioned include salts, especially the chloride or methyl sulfate, of diacyloxyethyldimethylammonium, diacyloxyethylhydroxyethylmethylammonium, monoacyloxyethyldihydroxyethylmethylammonium, triacyloxyethylmethylammonium or monoacyloxyethylhydroxyethyldimethylammonium, and mixtures thereof. The acyl groups preferably contain 14 to 18 carbon atoms and are derived more particularly from a plant oil such as palm oil or sunflower oil. When the compound contains several acyl groups, these groups may be identical or different.

These products are obtained, for example, by direct esterification of triethanolamine, trilsopropanolamine, an alkyldiethanolamine or an alkyldilsopropanolamine, which are optionally oxyalkylenated, with fatty acids or with mixtures of fatty acids of plant or animal origin, or by transesterification of the methyl esters thereof. This esterification is followed by quaternization by means of an alkylating agent such as an alkyl halide, preferably methyl or ethyl halide, a dialkyl sulfate, preferably dimethyl or diethyl sulfate, methyl methanesulfonate, methyl para-toluenesulfonate, glycol chlorohydrin or glycerol chlorohydrin.

Such compounds are sold, for example, under the names Dehyquart® by the company Henkel, Stepanquat® by the company Stepan, Noxamium® by the company CECA or Rewoquat® WE 18 by the company Rewo-Witco.

The composition according to the invention may contain, for example, a mixture of quaternary ammonium monoester, diester and triester salts with a weight majority of diester salts.

Use may also be made of the ammonium salts containing at least one ester function that are described in patents U.S. Pat. Nos. 4,874,554 and 4,137,180.

Use may also be made of the behenoylhydroxypropyltrimethylammonium chloride sold, for example, by the company KAO under the name Quartamin BTC 131.

Preferably, the ammonium salts containing at least one ester function contain two ester functions.

Among the cationic surfactants, it is more particularly preferred to choose cetyltrimethylammonium, behenyltrimethylammonium and dipalmitoylethylhydroxyethyl-methylammonium salts, and mixtures thereof, and more particularly behenyl-trimethylammonium chloride, cetyltrimethylammonium chloride, and dipalmitoylethylhydroxyethylammonium methosulfate, and mixtures thereof.

Preferably, the surfactant(s) is/are chosen from anionic surfactants, nonionic surfactants and mixtures thereof, preferentially from sulfated anionic surfactants, such as alkyl sulfates, ethoxylated C8-C24 fatty alcohols comprising from 1 to 200 ethylene oxide groups, ethoxylated C8-C30 fatty acid esters of sorbitan having from 1 to 30 ethylene oxide units, ($C_6$-$C_{24}$ alkyl)polyglycosides, and mixtures thereof.

More preferentially, the surfactant(s) is/are chosen from nonionic surfactants, better still from ethoxylated $C_8$-$C_{24}$ fatty alcohols comprising from 1 to 200 ethylene oxide groups, ($C_6$-$C_{24}$ alkyl)polyglycosides, and mixtures thereof.

When the composition comprises one or more surfactants, with preference, the total content of surfactant(s) in the composition preferably ranges from 0.01% to 15% by weight, more preferentially from 0.1% to 10% by weight, better still from 0.5% to 8% by weight, even better still from 1% to 6% by weight, relative to the total weight of the composition.

Sequestrant

The composition according to the invention may comprise one or more sequestrants (or chelating agents).

Preferably, the composition according to the invention comprises at least one sequestrant.

The definition of a "sequestrant" (or "chelating agent") is well known to those skilled in the art and refers to a compound or a mixture of compounds capable of forming a chelate with a metal Ion. A chelate is an inorganic complex in which a compound (the sequestrant or chelating agent) is coordinated to a metal ion, i.e. It forms one or more bonds with the metal ion (formation of a ring including the metal ion).

A sequestrant (or chelating agent) generally comprises at least two electron-donating atoms which enable the formation of bonds with the metal ion.

Within the context of the present invention, the sequestrant(s) may be chosen from carboxylic acids, preferably aminocarboxylic acids, phosphonic acids, preferably aminophosphonic acids, polyphosphoric acids, preferably linear polyphosphoric acids, salts thereof, and derivatives thereof.

The salts are in particular alkali metal, alkaline-earth metal, ammonium and substituted ammonium salts. The following compounds may be mentioned as examples of sequestrants based on carboxylic acids: diethylenetriaminepentaacetic acid (DTPA), ethylenediaminedisuccinic acid (EDDS) and trisodium ethylenediaminedisuccinate such as Octaquest E30 from OCTEL, ethylenediaminetetraacetic acid (EDTA), and its salts such as disodium EDTA, tetrasodium EDTA, ethylenediamine-N,N'-diglutaric acid (EDDG), glycinamide-N,N'-disuccinic acid (GADS), 2-hydroxypropylenediamine-N,N'-disuccinic acid (HPDDS), ethylenediamine-N,N'-bis(ortho-hydroxyphenylacetic acid) (EDDHA), N,N'-bis(2-hydroxybenzyl)ethylenediamine-N, N'-diacetic acid (HBED), nitrilotriacetic acid (NTA), methylglycinediacetic acid (MGDA), N-2-hydroxyethyl-N,N-diacetic acid and glyceryliminodiacetic acid (as described in documents EP-A-317,542 and EP-A-399,133), iminodiacetic acid-N-2-hydroxypropylsulfonic acid and aspartic acid-N-carboxymethyl-N-2-hydroxypropyl-3-sulfonic acid (as described in EP-A-516,102), beta-alanine-N,N'-diacetic acid, aspartic acid-N,N'-diacetic acid, aspartic acid-N-monoacetic acid (described in EP-A-509,382), chelating agents based on iminodisuccinic acid (IDSA) (as described in EP-A-509,382), ethanoldiglycine acid, phosphonobutanetricarboxylic acid such as the compound sold by Bayer under the reference Bayhibit AM, and N,N-dicarboxymethylglutamic acid and salts thereof such as tetrasodium glutamate diacetate (GLDA) such as Dissolvine GL38 or 45S from Akzo Nobel.

The following compounds may be mentioned as examples of chelating agents based on mono- or polyphosphonic acid: diethylenetriaminepenta(methylenephosphonic acid) (DTPMP), ethane-1-hydroxy-1,1,2-triphosphonic acid (E1HTP), ethane-2-hydroxy-1,1,2-triphosphonic acid (E2HTP), ethane-1-hydroxy-1,1-diphosphonic acid (EHDP), ethane-1,1,2-triphosphonic acid (ETP), ethylenediaminetetramethylenephosphonic acid (EDTMP), hydroxyethane-1,1-diphosphonic acid (HEDP, or etidronic acid), and salts such as disodium etidronate, tetrasodium etidronate.

The following compounds may be mentioned as examples of chelating agents based on polyphosphoric acid: sodium tripolyphosphate (STP), tetrasodium diphosphate, hexametaphosphoric acid, sodium metaphosphate, phytic acid.

According to a particular embodiment, the sequestrant(s) useful according to the invention is/are phosphorus-based sequestrants, i.e. sequestrants which comprise one or more phosphorus atoms, preferably at least two phosphorus atoms.

The phosphorus-based sequestrants used in the composition according to the invention are preferably chosen from:

- inorganic phosphorus-based derivatives preferably chosen from alkali metal or alkaline-earth metal, preferably alkali metal, phosphates and pyrophosphates, such as sodium pyrophosphate, potassium pyrophosphate, sodium pyrophosphate decahydrate; and alkali metal or alkaline-earth metal, preferably alkali metal, polyphosphates, such as sodium hexametaphosphate, sodium polyphosphate, sodium tripolyphosphate, sodium trimetaphosphate; which are optionally hydrated, and mixtures thereof;
- organic phosphorus-based derivatives, such as organic (poly)phosphates and (poly)phosphonates, such as etidronic acid and/or alkali metal or alkaline-earth metal salts thereof, for instance tetrasodium etidronate, disodium etidronate, and mixtures thereof.

Preferably, the phosphorus-based sequestrant(s) is/are chosen from linear or cyclic compounds comprising at least two phosphorus atoms bonded together covalently via at least one linker L comprising at least one oxygen atom and/or at least one carbon atom.

The phosphorus-based sequestrant(s) may be chosen from inorganic phosphorus-based derivatives, preferably comprising at least 2 phosphorus atoms. More preferentially, the phosphorus-based sequestrant(s) is/are chosen from alkali metal or alkaline-earth metal pyrophosphates, better still from alkali metal pyrophosphates, in particular sodium pyrophosphate (also known as tetrasodium pyrophosphate).

The phosphorus-based sequestrant(s) may be chosen from organic phosphorus-based derivatives, preferably comprising at least 2 phosphorus atoms. More preferentially, the phosphorus-based sequestrant(s) is/are chosen from etidronic acid (also known as 1-hydroxyethane-1,1-diphosphonic acid) and/or alkali metal or alkaline-earth metal, preferably alkali metal, salts thereof, for instance tetrasodium etidronate and disodium etidronate.

Thus, preferably, the phosphorus-based sequestrant(s) is/are chosen from alkali metal pyrophosphates, etidronic acid and/or alkali metal salts thereof, and a mixture of these compounds.

Particularly preferably, the phosphorus-based sequestrant(s) is/are chosen from tetrasodium etidronate, disodium etidronate, etidronic acid, tetrasodium pyrophosphate, and a mixture of these compounds.

According to the present invention, the sequestrants are preferably chosen from diethylenetriaminepentaacetic acid (DTPA) and salts thereof, diethylenediaminetetraacetic acid (EDTA) and salts thereof, ethylenediaminedisuccinic acid (EDDS) and salts thereof, etidronic acid and salts thereof, N,N-dicarboxymethylglutamic acid and salts thereof, N,N-dicarboxymethylglutamic acid and salts thereof (GLDA), and mixtures thereof.

Among the salts of these compounds, the alkali metal salts and especially the sodium or potassium salts are preferred.

When the composition comprises one or more sequestrants, the total content of the sequestrant(s) preferably ranges from 0.001% to 15% by weight, more preferentially from 0.005% to 10% by weight, better still from 0.01% to 8% by weight, even better still from 0.05% to 5% by weight, relative to the total weight of the composition.

Thickener

The composition according to the present invention can comprise one or more thickeners.

For the purposes of the present invention, the term thickener is understood to mean an agent which, by its presence in the composition, makes it possible to increase the viscosity of said composition by at least 10 cPs, preferably by at least 200 cPs, at 25° C. and at a shear rate of 1 $s^{-1}$. This viscosity can be measured using a cone/plate viscometer (Haake R600 rheometer or the like).

The thickener(s) can in particular be chosen from sodium chloride, fatty acid amides obtained from ($C_{10}$-$C_{30}$) carboxylic acid (coconut acid monoisopropanolamide, diethanolamide or monoethanolamide, oxyethylenated alkyl ether carboxylic acid monoethanolamide), thickening polymers other than associative polymers and in particular nonionic cellulosic polymers (hydroxyethylcellulose, hydroxypropylcellulose, carboxymethylcellulose), guar gum and nonionic derivatives thereof (hydroxypropyl guar), gums of microbial origin (xanthan gum, scleroglucan gum), crosslinked or non-crosslinked homopolymers and copolymers based on acrylic acid, on methacrylic acid or on acrylamidopropanesulfonic acid, associative polymers, and mixtures thereof.

The thickening polymers may be chosen from associative polymers and non-associative polymers.

For the purposes of the present invention, the term "associative polymers" means water-soluble polymers that are capable, in an aqueous medium, of reversibly associating with each other or with other molecules.

Their chemical structure comprises hydrophilic regions and hydrophobic regions characterized by at least one fatty chain preferably containing from 10 to 30 carbon atoms.

The associative polymer(s) that can be used according to the invention can be of anionic, cationic, amphoteric or nonionic type, such as the polymers sold under the names Pemulen TR1 or TR2 by Goodrich (INCI: Acrylates/C10-30 Alkyl Acrylate Crosspolymer), Salcare SC90 by Ciba, ACULYN 22, 28, 33, 44 or 46 by Rohm & Haas and Elfacos T210 and T212 by Akzo.

Preferably, the associative polymers may be chosen from cellulosic polymers.

Preferably, the associative polymer(s) is/are chosen from celluloses modified with groups including at least one fatty chain.

Preferentially, the associative polymer(s) may be chosen from hydroxyethylcelluloses modified with groups including at least one fatty chain, such as alkyl, arylalkyl or alkylaryl groups, or mixtures thereof, and in which the alkyl groups are preferably $C_8$-$C_{22}$, and hydroxyethylcelluloses modified with polyalkylene glycol alkylphenyl ether groups, and mixtures thereof, preferably cetylhydroxyethylcellulose.

Preferentially, the associative polymer(s) may be chosen from quaternized cellulose derivatives, preferably chosen from quaternized hydroxyethylcelluloses modified with groups comprising at least one fatty chain, such as linear or branched alkyl groups, linear or branched arylalkyl groups, or linear or branched alkylaryl groups, preferably linear or branched alkyl groups, these groups comprising at least 8 carbon atoms, in particular from 8 to 30 carbon atoms, better still from 10 to 24, or even from 10 to 14, carbon atoms; or mixtures thereof, and even better still polyquaternium-67.

The thickening polymers may also be chosen from non-associative polymers, and in particular nonionic cellulosic polymers (hydroxyethylcellulose, hydroxypropylcellulose, carboxymethylcellulose), guar gum and nonionic derivatives thereof (hydroxypropyl guar), gums of microbial origin (xanthan gum, scleroglucan gum), crosslinked or non-crosslinked homopolymers and copolymers based on acrylic acid, on methacrylic acid or on acrylamidopropanesulfonic acid, and mixtures thereof.

Among the non-associative polymers, it is also possible to choose an anionic (meth)acrylic polymer such as (meth) acrylic acid homopolymers or copolymers. Mention may be made, for example, of compounds with the INCI name Carbomer.

Preferably, the non-associative polymers are chosen from guar gums, xanthan gum, and (meth)acrylic acid homopolymers or copolymers.

According to a preferred embodiment, the thickener is chosen from associative or non-associative thickening polymers.

According to a preferred embodiment, the thickener is chosen from non-associative thickening polymers, more preferentially from guar gums.

The guar gums that can be used according to the invention may be nonionic or cationic.

According to the invention, use may be made of chemically modified or unmodified nonionic guar gums.

The unmodified nonionic guar gums are, for example, the products sold under the name Vidogum GH 175 by the company Unipectine and under the names Meypro-Guar 50 and Jaguar C by the company Rhodia Chimie.

The modified nonionic guar gums that may be used according to the invention are preferably modified with C1-C6 hydroxyalkyl groups.

Among the hydroxyalkyl groups, mention may be made, by way of example, of hydroxymethyl, hydroxyethyl, hydroxypropyl and hydroxybutyl groups.

These guar gums are well known from the prior art and may be prepared, for example, by reacting corresponding alkene oxides, for instance, propylene oxides, with the guar gum so as to obtain a guar gum modified with hydroxypropyl groups.

The degree of hydroxyalkylation, which corresponds to the number of alkylene oxide molecules consumed by the number of free hydroxyl functions present on the guar gum, preferably ranges from 0.4 to 1.2.

Such nonionic guar gums optionally modified with hydroxyalkyl groups are sold, for example, under the trade names Jaguar HP8, Jaguar HP60 and Jaguar HP120, Jaguar DC 293 and Jaguar HP 105 by the company Meyhall, or under the name Galactasol 4H4FD2 by the company Aqualon.

Also suitable for use are nonionic guar gums modified with hydroxyalkyl groups, more especially hydroxypropyl groups, modified with groups comprising at least one $C_6$-$C_{30}$ fatty chain. Examples of such compounds that may be mentioned include, inter alia, the product Esafior HM 22® ($C_{22}$ alkyl chain) sold by the company Lamberti, and the products RE210-18® ($C_{14}$ alkyl chain) and RE205-1® ($C_{20}$ alkyl chain) sold by the company Rhône-Poulenc.

The cationic guar gums that may more particularly be used according to the invention are guar gums comprising trialkylammonium cationic groups. Preferably, 2% to 30% and more preferentially still 5% to 20% by number of the hydroxyl functions of these guar gums bear trialkylammonium cationic groups.

Among these trialkylammonium groups, mention may most particularly be made of the trimethylammonium and triethylammonium groups.

Even more preferentially, these groups represent from 5% to 20% by weight relative to the total weight of the modified guar gum.

According to the invention, a guar gum modified with 2,3-epoxypropyltrimethylammonium chloride is preferably used.

These guar gums modified with cationic groups are products already known per se and are, for example, described in patents U.S. Pat. Nos. 3,589,578 and 4,013,307. Such products are moreover notably sold under the trade names Jaguar C13 S, Jaguar C 15 and Jaguar C 17 by the company Meyhall.

Preferably, a nonionic guar gum is used and, among these nonionic guar gums, more particularly guar gums modified with hydroxyalkyl groups.

When the composition comprises one or more thickeners, the total content of thickener(s) preferably ranges from 0.01% to 20% by weight, more preferentially from 0.05% to 10% by weight, better still from 0.1% to 5% by weight, even better still from 0.2% to 3% by weight, relative to the total weight of the composition.

When the composition comprises one or more thickening polymers, the total content of thickening polymer(s) preferably ranges from 0.01% to 20% by weight, more preferentially from 0.05% to 10% by weight, better still from 0.1% to 5% by weight, even better still from 0.2% to 3% by weight, relative to the total weight of the composition.

When the composition comprises one or more guar gums, the total content of guar gum(s) preferably ranges from 0.01% to 20% by weight, more preferentially from 0.05% to 10% by weight, better still from 0.1% to 5% by weight, even better still from 0.2% to 3% by weight, relative to the total weight of the composition.

Alkaline Agent

The composition according to the present invention may comprise one or more mineral, organic or hybrid alkaline agents.

Preferably, the composition according to the present invention comprises one or more mineral, organic or hybrid alkaline agents.

For the purposes of the present invention, the terms "alkaline agent" and "basifying agent" are used interchangeably.

The mineral basifying agent(s) is/are preferably chosen from aqueous ammonia, alkali metal carbonates or bicarbonates such as sodium (hydrogen)carbonate and potassium (hydrogen)carbonate, alkali metal or alkaline-earth metal phosphates such as sodium phosphates or potassium phosphates, sodium or potassium hydroxides, and mixtures thereof.

The organic basifying agent(s) is/are preferably chosen from alkanolamines, amino acids, organic amines, oxyethylenated and/or oxypropylenated ethylenediamines, 1,3-diaminopropane, 1,3-diamino-2-propanol, spermine or spermidine and mixtures thereof.

The term "alkanolamine" is intended to mean an organic amine comprising a primary, secondary or tertiary amine function, and one or more linear or branched $C_1$-$C_8$ alkyl groups bearing one or more hydroxyl radicals.

Organic amines chosen from alkanolamines such as monoalkanolamines, dialkanolamines or trialkanolamines comprising one to three Identical or different $C_1$-$C_4$ hydroxyalkyl radicals are in particular suitable for carrying out the invention.

In particular, the alkanolamine(s) is/are chosen from monoethanolamine (MEA), diethanolamine, triethanolamine, monoisopropanolamine, diisopropanolamine, N,N-dimethylethanolamine, 2-amino-2-methyl-1-propanol, triisopropanolamine, 2-amino-2-methyl-1,3-propanediol, 3-amino-1,2-propanediol, 3-dimethylamino-1,2-propanediol, tris(hydroxymethyl)aminomethane and mixtures thereof.

Advantageously, the amino acids are basic amino acids comprising an additional amine function. Such basic amino acids are preferably chosen from histidine, lysine, arginine, omithine and citrulline.

The organic amine may also be chosen from organic amines of heterocyclic type. Besides histidine that has already been mentioned in the amino acids, mention may in particular be made of pyridine, piperidine, imidazole, triazole, tetrazole and benzimidazole. The organic amine may also be chosen from amino acid dipeptides. As amino acid dipeptides that may be used in the present invention, mention may notably be made of camosine, anserine and balenine. The organic amine may also be chosen from compounds comprising a guanidine function. As amines of this type other than arginine that may be used in the present invention, mention may especially be made of creatine, creatinine, 1,1-dimethylguanidine, 1,1-diethylguanidine, glycocyamine, metformin, agmatine, n-amidoalanine, 3-guanidinopropionic acid, 4-guanidinobutyric acid and 2-([amino(imino)methyl]amino)ethane-1-sulfonic acid.

Use may be made in particular of guanidine carbonate or monoethanolamine hydrochloride as hybrid compounds.

The alkaline agent(s) that may be used according to the invention is/are preferably chosen from alkanolamines such as monoethanolamine, diethanolamine, triethanolamine; aqueous ammonia, carbonates or bicarbonates such as sodium (hydrogen)carbonate and potassium (hydrogen)carbonate and mixtures thereof, more preferentially from alkanolamines and aqueous ammonia, better still from alkanolamines.

When the composition comprises at least one alkaline agent, the total content of the alkaline agent(s) preferably ranges from 0.1% to 40% by weight, more preferentially from 0.5% to 30% by weight, better still from 1% to 20% by weight, even better still from 2% to 10% by weight, relative to the total weight of the composition.

According to one embodiment, the pH of the composition comprising at least one alkaline agent is between 8 and 13; preferably between 9.0 and 12.

The pH of the composition may be adjusted to the desired value by means of acidic or alkaline agent(s) commonly used in the dyeing of keratin fibres, such as those described hereinabove, or alternatively using buffer systems known to those skilled in the art.

According to a particular embodiment, the composition according to the invention comprises:

2-(methoxymethyl)benzene-1,4-diamine of formula (I), one of its addition salts, its solvates and/or the solvates of its salts:

(I)

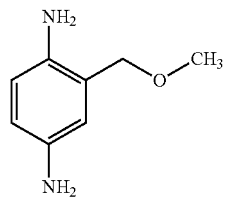

at least one coupler chosen from: 6-hydroxybenzomorpholine of formula (II), its addition salts, its solvates and/or the solvates of its salts, and mixtures thereof;

(II)

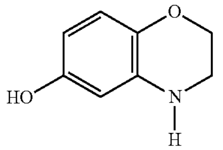

at least one coupler chosen from: 2-amino-5-ethylphenol of formula (III), its addition salts, its solvates and/or the solvates of its salts, and mixtures thereof;

(III)

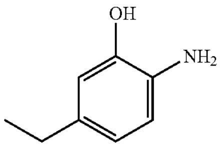

at least one fatty substance,
at least one surfactant;
at least one sequestrant; and
at least one alkaline agent.

Solvents

The composition according to the invention may also comprise at least one organic solvent.

Examples of organic solvents that may be mentioned include linear or branched $C_2$ to C4 alkanols, such as ethanol and isopropanol; polyols and polyol ethers, for instance 2-butoxyethanol, glycerol, propylene glycol, dipropylene glycol, propylene glycol monomethyl ether, diethylene glycol monomethyl ether and monoethyl ether, and also aromatic alcohols or ethers, for instance benzyl alcohol or phenoxyethanol, and mixtures thereof.

The organic solvent(s) may be present in an amount ranging from 0.01% to 30% by weight, preferably ranging from 2% to 25% by weight, relative to the total weight of the composition.

In addition, the composition according to the invention is preferably an aqueous composition. The composition preferably comprises water in an amount of greater than or equal to 5% by weight, preferably greater than or equal to 10% by weight, and better still greater than or equal to 15% by weight, relative to the total weight of the composition.

Additives

The composition according to the invention may optionally comprise one or more additives, different from the compounds of the invention and among which mention may be made of cationic, anionic, nonionic or amphoteric polymers or mixtures thereof, other than those mentioned hereinabove, antidandruff agents, anti-seborrhoeic agents, agents for preventing hair loss and/or for promoting hair regrowth, vitamins and provitamins including panthenol, sunscreens, mineral or organic pigments, plasticizers, solubilizers, opacifiers or pearlescent agents, antioxidants, hydroxy acids, fragrances, and preservatives.

Of course, those skilled in the art will take care to choose this or these optional additional compound(s) so that the advantageous properties intrinsically associated with the composition according to the invention are not, or not substantially, detrimentally affected by the envisioned addition(s).

The above additives may generally be present in an amount, for each of them, of between 0 and 20% by weight relative to the total weight of the ready-to-use composition.

According to a particular embodiment, the composition according to the invention does not comprise chemical oxidizing agents.

The term "chemical oxidizing agent" means an oxidizing agent other than atmospheric oxygen.

Process

The present invention also relates to a process for dyeing keratin fibres, preferably the hair, which comprises the application to said keratin fibres of an effective amount of a composition as described previously.

The composition may be applied to wet or dry keratin fibres. On conclusion of the treatment, the keratin fibres are optionally rinsed with water, optionally washed with a shampoo and then rinsed with water, before being dried or left to dry.

According to one embodiment, the composition according to the invention Is mixed at the moment of use with a composition comprising at least one chemical oxidizing agent, preferably hydrogen peroxide.

Preferably, the pH of such resulting composition is between 8 and 11, preferably between 9 and 10.7.

According to another embodiment, the composition according to the invention comprises at least one oxidizing agent, preferably hydrogen peroxide.

According to this embodiment, at the moment of use, the composition according to the invention results from the mixing of at least two compositions:

- a dye composition comprising
  - 2-(methoxymethyl)benzene-1,4-diamine of formula (I), its addition salts, its solvates and/or the solvates of its salts:

(I)

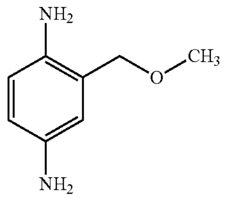

- at least one coupler chosen from: 6-hydroxybenzomorpholine of formula (II), its addition salts, its solvates and/or the solvates of its salts, and mixtures thereof;

(II)

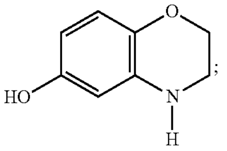

- and
  - at least one coupler chosen from 2-amino-5-ethylphenol of formula (III), its addition salts, Its solvates and/or the solvates of its salts, and mixtures thereof;

(III)

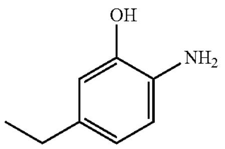

- and an oxidizing composition comprising one or more chemical oxidizing agents, preferably hydrogen peroxide.

According to one embodiment, the process according to the invention comprises a step of mixing the composition according to the invention with an oxidizing composition comprising at least one chemical oxidizing agent. This mixing step is preferably performed at the moment of use, just before applying the composition resulting from the mixing to the hair.

According to this embodiment, the process for dyeing keratin fibres, preferably the hair, according to the invention, comprises the step of applying, to the keratin fibres, a composition resulting from the mixing, at the moment of use, of at least two compositions:

a) a dye composition comprising 2-(methoxymethyl)benzene-1,4-diamine of formula (I), Its addition salts, Its solvates and/or the solvates of its salts, and mixtures thereof;

(I)

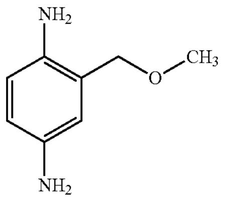

at least one coupler chosen from: 6-hydroxybenzomorpholine of formula (II), Its addition salts, Its solvates and/or the solvates of its salts, and mixtures thereof;

(II)

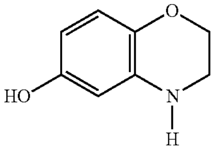

at least one coupler chosen from 2-amino-5-ethylphenol of formula (III), its addition salts, its solvates and/or the solvates of its salts, and mixtures thereof;

(III)

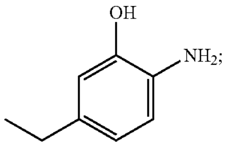

b) an oxidizing composition comprising one or more chemical oxidizing agents, preferably hydrogen peroxide.

In a preferred embodiment, the process for dyeing keratin fibres, preferably the hair, according to the invention, comprises the step of applying, to the keratin fibres, a composition resulting from the mixing, at the moment of use, of at least two compositions:

a) a dye composition comprising 2-(methoxymethyl)benzene-1,4-diamine of formula (I), its addition salts, its solvates and/or the solvates of its salts, and mixtures thereof;

(I)

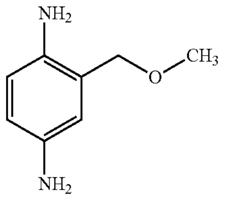

at least one coupler chosen from: 6-hydroxybenzomorpholine of formula (II), its addition salts, its solvates and/or the solvates of its salts, and mixtures thereof;

(II)

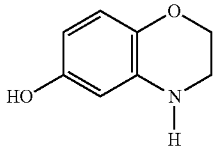

at least one coupler chosen from 2-amino-5-ethylphenol of formula (III), its addition salts, its solvates and/or the solvates of its salts, and mixtures thereof;

(III)

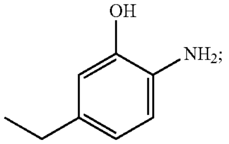

at least one fatty substance, at least one surfactant;

at least one sequestrant; and at least one alkaline agent; and b) an oxidizing composition comprising one or more chemical oxidizing agents, preferably hydrogen peroxide.

More particularly, the chemical oxidizing agent(s) is/are chosen from hydrogen peroxide, urea peroxide, alkali metal bromates or ferricyanides, peroxygenated salts, for instance persulfates, perborates, peracids and precursors thereof and percarbonates of alkali metals or alkaline-earth metals, and mixtures thereof. The oxidizing agent is preferably chosen from hydrogen peroxide.

The oxidizing composition Is preferably an aqueous composition. In particular, it comprises more than 5% by weight of water, preferably more than 10% by weight of water and even more advantageously more than 20% by weight of water.

It may also comprise one or more organic solvents chosen from those listed previously; these solvents more particularly representing, when they are present, from 1% to 40% by weight and preferably from 5% to 30% by weight, relative to the weight of the oxidizing composition.

The oxidizing composition also preferably comprises one or more acidifying agents. Among the acidifying agents, examples that may be mentioned include mineral or organic acids, for instance hydrochloric acid, orthophosphoric acid, sulfuric acid, carboxylic acids, for instance acetic acid, tartaric acid, citric acid or lactic acid, and sulfonic acids.

The oxidizing composition may additionally comprise fatty substances such as those described hereinabove, preferably chosen from fatty alcohols, liquid hydrocarbons comprising more than 16 carbon atoms and mixtures thereof, surfactants and polymers.

Usually, the pH of the oxidizing composition, when it is aqueous, is less than 7.

Preferably, the oxidizing composition comprises hydrogen peroxide as oxidizing agent, in aqueous solution, the concentration of which ranges, more particularly, from 0.1% to 50%, more particularly between 0.5% and 20% and even more preferentially between 1% and 15% by weight, relative to the weight of the oxidizing composition.

Preferably, at least one of the (dye or oxidizing) compositions is aqueous.

Kit

Another subject of the invention is a multi-compartment device, preferably comprising two compartments, for dyeing keratin fibres, preferably the hair, at least a first compartment containing the dye composition according to the invention and at least a second compartment containing an oxidizing composition as described above.

The compositions of the device according to the invention are packaged in separate compartments, optionally accompanied by suitable application means which may be identical or different, such as fine brushes, coarse brushes or sponges.

The device mentioned above may also be equipped with a means for dispensing the desired mixture on the hair, for instance the devices described in patent FR 2 586 913.

Finally, the present invention relates to the use of a composition as described above, for dyeing keratin fibres, and in particular the hair.

The following examples serve to illustrate the invention without, however, being limiting in nature.

EXAMPLES

In the examples that follow, all the amounts are given as weight percentage of active material (AM) relative to the total weight of the composition (unless stated otherwise).

Example 1

Dyeing Composition

Composition A1 according to the present invention and comparative composition A2 were prepared using the ingredients of which the contents are indicated in the table below:

TABLE 1

| | A1 (invention) | A2 (comparative) |
|---|---|---|
| 2-OLEAMIDO-1,3-OCTADECANEDIOL | 0.01 | 0.01 |
| AMMONIUM HYDROXIDE | 4.6 | 4.6 |
| EDTA | 0.2 | 0.2 |
| MONOETHANOLAMINE | 0.63 | 0.63 |
| m-AMINOPHENOL | 0.55 | 0.55 |
| 2,4-DIAMINOPHENOXYETHANOL HCl | 0.14 | 0.14 |
| 6-HYDROXYINDOLE | 0.1 | 0.1 |
| 2-METHOXYMETHYL-P-PHENYLENEDIAMINE | $1.25 \cdot 10^{-2}$ mol | — |
| HYDROXYETHYL-p-PHENYLENEDIAMINE SULFATE | — | $1.25 \cdot 10^{-2}$ mol |
| SODIUM METABISULFITE | 0.71 | 0.71 |
| 2-AMINO-5-ETHYLPHENOL HCL | 0.57 | 0.57 |
| HYDROXYBENZOMORPHOLINE | 0.5 | 0.5 |
| 2-AMINO-3-HYDROXYPYRIDINE | 0.04 | 0.04 |
| N,N-BIS(2-HYDROXYETHYL)-p-PHENYLENEDIAMINE SULFATE | 0.14 | 0.14 |
| CETEARYL ALCOHOL | 16.2 | 16.2 |
| OLEYL ALCOHOL | 2.7 | 2.7 |
| FRAGRANCE | 0.5 | 0.5 |
| HEXADIMETHRINE CHLORIDE | 3 | 3 |
| OLETH-30 | 3.6 | 3.6 |
| OLEIC ACID | 2.7 | 2.7 |
| Water | qs 100 | qs 100 |

Oxidizing Composition

The oxidizing composition B was prepared from the ingredients of which the contents are indicated in the table below:

TABLE 2

| | B |
|---|---|
| SODIUM SALICYLATE | 0.035 |
| TETRASODIUM PYROPHOSPHATE | 0.04 |
| HYDROGEN PEROXIDE | 6 |
| CETEARYL ALCOHOL et CETEARETH-25 | 2.85 |
| TETRASODIUM ETIDRONATE | 0.06 |
| PHOSPHORIC ACID | QS PH 2.2 |
| TRIDECETH-2 CARBOXAMIDE MEA | 0.85 |
| GLYCERIN | 0.5 |
| Water | qs 100 |

Dyeing Protocol

The dye compositions A1 and A2 are each mixed with the oxidizing composition B in a 1+1.5 weight ratio.

Each of the mixtures is applied to locks of hair containing 90% natural white (NW) hair and 90% permanent-waved natural white (PW) hair in a proportion of 5 g of mixture per 1 g of hair.

After a leave-on time of 30 minutes on a hot plate at 27° C., the hair Is rinsed, washed with L'Oréal Professionnel Pro Classics universal concentrated shampoo, diluted to 10%, and dried.

Results

The colouring of the hair is evaluated in the L*a*b* system, using a Konica Minolta CM-3600A spectrocolorimeter (illuminant D65, angle 10°, specular component included) in the CIELab system.

In this system, L* represents the lightness. The lower the value of L*, the darker and more powerful the colouring obtained. The chromaticity is measured by the values a* and b*, a* representing the red/green axis and b* the yellow/blue axis.

The selectivity Is represented by the colour difference ΔE between the locks of dyed natural hair (NW) and dyed permanent-waved hair (PW): the smaller the value of ΔE, the better the selectivity.

The value of ΔE is calculated according to the following equation:

$$\Delta E=\sqrt{(L^*-L_0^*)^2+(a^*-a_0^*)^2+(b^*-b_0^*)^2}$$

In this equation, L*, a* and b* represent the values measured on dyed natural hair (NW) and $L_0^*$, $a_0^*$ and $b_0^*$ represent the values measured on dyed sensitized hair (PW).

The results are summarized in the following table.

TABLE 3

| | ΔE |
|---|---|
| Process A1 + B (invention) | 0.80 |
| Process A2 + B (comparative) | 4.11 |

The composition according to the invention leads to a lower value of ΔE, thus to a better selectivity, compared to the comparative composition according to the prior art.

Example 2

Dyeing Composition

Composition A3 according to the present invention and comparative composition A4 were prepared using the ingredients of which the contents are indicated in the table below:

TABLE 4

| | A3 (invention) | A4 (comparative) |
|---|---|---|
| 2-OLEAMIDO-1,3-OCTADECANEDIOL | 0.01 | 0.01 |
| AMMONIUM HYDROXIDE | 4.6 | 4.6 |
| EDTA | 0.2 | 0.2 |
| MONOETHANOLAMINE | 0.63 | 0.63 |
| m-AMINOPHENOL | 0.55 | 0.55 |
| 2,4-DIAMINOPHENOXYETHANOL HCl | 0.14 | 0.14 |
| 6-HYDROXYINDOLE | 0.1 | 0.1 |
| 2-METHOXYMETHYL-P-PHENYLENEDIAMINE | 1.9 | 1.9 |
| SODIUM METABISULFITE | 0.71 | 0.71 |
| 2-AMINO-5-ETHYLPHENOL HCL | 3.3 mmol | 6.6 mmol |
| HYDROXYBENZOMORPHOLINE | 3.3 mmol | — |
| 2-AMINO-3-HYDROXYPYRIDINE | 0.04 | 0.04 |
| N,N-BIS(2-HYDROXYETHYL)-p-PHENYLENEDIAMINE SULFATE | 0.14 | 0.14 |
| CETEARYL ALCOHOL | 16.2 | 16.2 |
| OLEYL ALCOHOL | 2.7 | 2.7 |
| FRAGRANCE | 0.5 | 0.5 |
| HEXADIMETHRINE CHLORIDE | 3 | 3 |
| OLETH-30 | 3.6 | 3.6 |
| OLEIC ACID | 2.7 | 2.7 |
| Water | qs 100 | qs 100 |
| pH | 10.2 +/− 0.2 | 10.2 +/− 0.2 |

Oxidizing Composition

The oxidizing composition B was prepared from the ingredients of which the contents are indicated in the table below:

TABLE 5

| | B |
|---|---|
| SODIUM SALICYLATE | 0.035 |
| TETRASODIUM PYROPHOSPHATE | 0.04 |
| HYDROGEN PEROXIDE | 6 |
| CETEARYL ALCOHOL et CETEARETH-25 | 2.85 |
| TETRASODIUM ETIDRONATE | 0.06 |
| PHOSPHORIC ACID | QS PH 2.2 |
| TRIDECETH-2 CARBOXAMIDE MEA | 0.85 |
| GLYCERIN | 0.5 |
| Water | qs 100 |

Dyeing Protocol

The dye compositions A3 and A4 are each mixed with the oxidizing composition B in a 1+1.5 weight ratio; the resulting mixtures having a pH of 9.7+/−0.2.

Each of the mixtures is applied to locks of hair containing 90% permanent-waved natural white (PW) hair and sensitized (SA20) hair in a proportion of 5 g of mixture per 1 g of hair.

After a leave-on time of 30 minutes on a hot plate at 27° C., the hair Is rinsed, washed with L'Oréal Professionnel Pro Classics universal concentrated shampoo, diluted to 10%, and dried.

Results

The colouring of the hair is evaluated in the L*a*b* system, using a Konica Minolta CM-3600A spectrocolorimeter (illuminant D65, angle 10°, specular component included) in the CIELab system.

In this system, L* represents the lightness. The lower the value of L*, the darker and more powerful the colouring obtained. The chromaticity is measured by the values a* and b*, a* representing the red/green axis and b* the yellow/blue axis.

The selectivity is represented by the colour difference ΔE between the locks of dyed permanent-waved hair (PW) and sensitized (SA20) hair the smaller the value of ΔE, the better the selectivity.

The value of ΔE is calculated according to the following equation:

$$\Delta E=\sqrt{(L^*-L_0^*)^2+(a^*-a_0^*)^2+(b^*-b_0^*)^2}$$

In this equation, L*, a* and b* represent the values measured on dyed permanent-waved hair (PW) and $L_0^*$, $a_0^*$ and $b_0^*$ represent the values measured on dyed sensitized hair (SA20).

The results are summarized in the following table.

TABLE 6

| | | L | a | b | ΔE |
|---|---|---|---|---|---|
| Process A3 + B (invention) | PW | 17.22 | 0.78 | 0.66 | 0.29 |
| | SA20 | 16.95 | 0.68 | 0.64 | |
| Process A4 + B (comparative) | PW | 19.4 | 1.67 | 1.55 | 3.89 |
| | SA20 | 16.18 | 0.73 | −0.42 | |

The composition according to the invention leads to a lower value of ΔE, thus to a better selectivity, compared to the comparative composition according to the prior art.

The invention claimed is:

1. A composition comprising:

from 0.01% to 10% of 2-(methoxymethyl) benzene-1,4-diamine of formula (I), addition salts thereof, solvates thereof, solvates of its salts thereof, or mixtures of two or more thereof:

(I)

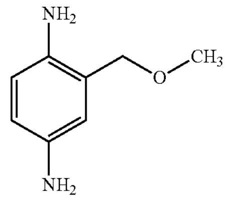

from 0.01% to 10% of at least one coupler chosen from 6-hydroxybenzomorpholine of formula (II), addition salts thereof, solvates thereof, solvates of its salts thereof, or mixtures of two or more thereof:

(II)

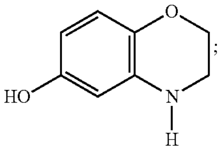

and from 0.01% to 10% of at least one coupler chosen from 2-amino-5-ethylphenol of formula (III), addition salts thereof, solvates thereof, solvates of its salts thereof, or mixtures of two or more thereof:

(III)

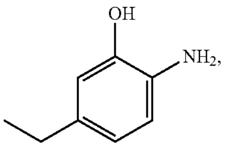

wherein all the amounts are by weight, relative to the total weight of the composition.

2. The composition of claim 1, wherein the total amount of couplers of formulae (II) and (III), addition salts thereof, solvates thereof, solvates of their salts thereof, or mixtures of two or more thereof ranges from 0.02% to 20% by weight, relative to the total weight of the composition.

3. The composition of claim 1, further comprising at least one fatty substance.

4. The composition of claim 3, wherein the at least one fatty substance comprises at least one liquid fatty substance.

5. The composition of claim 4, wherein the at least one liquid fatty substance is chosen from liquid hydrocarbons comprising more than 16 carbon atoms, plant oils, liquid fatty alcohols, liquid fatty esters, silicone oils, or mixtures of two or more thereof.

6. The composition of claim 3, wherein the at least one fatty substance comprises at least one solid fatty substance.

7. The composition of claim 6, wherein the at least one solid fatty substance is chosen from solid fatty acids; solid fatty alcohols; solid esters of fatty acids, of fatty alcohols, or of combinations of two or more thereof; waxes; ceramides; or mixtures of two or more thereof.

8. The composition of claim 1, further comprising at least one surfactant.

9. The composition of claim 1, further comprising at least one sequestrant.

10. The composition of claim 1, further comprising at least one alkaline agent.

11. The composition of claim 10, wherein the at least one alkaline agent is chosen from alkanolamines, aqueous ammonia, carbonates, bicarbonates, or mixtures of two or more thereof.

12. The composition of claim 1, wherein the composition is free of any chemical oxidizing agent.

13. The composition of claim 1, further comprising at least one chemical oxidizing agent.

14. A method for dyeing keratin fibers, comprising:

(a) mixing a dye composition (A) with an oxidizing composition (B), wherein the dye composition (A) comprises:

i) from 0.01% to 10% of 2-(methoxymethyl) benzene-1,4-diamine of formula (I), addition salts thereof, solvates thereof, solvates of its salts thereof, or mixtures of two or more thereof:

(I)

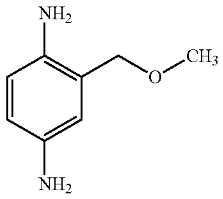

ii) from 0.01% to 10% of at least one coupler chosen from 6-hydroxybenzomorpholine of formula (II), addition salts thereof, solvates thereof, solvates of its salts thereof, or mixtures of two or more thereof:

(II)

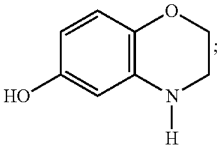

and iii) from 0.01% to 10% of at least one coupler chosen from 2-amino-5-ethylphenol of formula (III), addition salts thereof, solvates thereof, solvates of its salts thereof, or mixtures of two or more thereof:

(III)

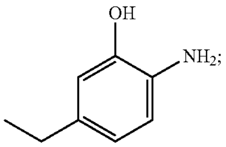

wherein all the amounts are by weight, relative to the total weight of the dye composition (A), and wherein the oxidizing composition (B) comprises at least one chemical oxidizing agent, and (b) applying the mixture to keratin fibers.

15. The method of claim 14, wherein the total amount of couplers of formulae (II) and (III), addition salts thereof, solvates thereof, solvates of their salts thereof, or mixtures of two or more thereof in dye composition (A) ranges from 0.02% to 20% by weight, relative to the total weight of the dye composition (A).

16. The method of claim 14, wherein dye composition (A) further comprises at least one fatty substance.

17. The method of claim 14, wherein dye composition (A) further comprises at least one sequestrant.

18. A kit comprising:

(i) a first compartment comprising a dye composition comprising:

from 0.01% to 10% of 2-(methoxymethyl) benzene-1,4-diamine of formula (I), addition salts thereof, solvates thereof, solvates of its salts thereof, or mixtures of two or more thereof:

(I)

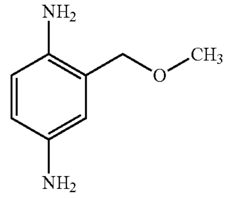

from 0.01% to 10% of at least one coupler chosen from 6-hydroxybenzomorpholine of formula (II), addition salts thereof, solvates thereof, solvates of its salts thereof, or mixtures of two or more thereof;

(II)

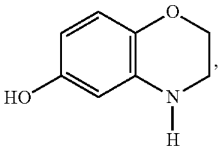

and from 0.01% to 10% of at least one coupler chosen from 2-amino-5-ethylphenol of formula (III), addition salts thereof, solvates thereof, solvates of its salts thereof, or mixtures of two or more thereof;

(III)

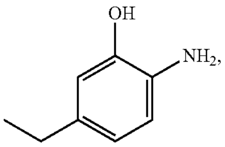

wherein all the amounts are by weight, relative to the total weight of the dye composition; and (ii) a second compartment comprising an oxidizing composition comprising at least one chemical oxidizing agent.

* * * * *